US011152119B2

(12) United States Patent
Wang et al.

(10) Patent No.: US 11,152,119 B2
(45) Date of Patent: Oct. 19, 2021

(54) CARE PATH ANALYSIS AND MANAGEMENT PLATFORM

(71) Applicant: HITACHI, LTD., Tokyo (JP)

(72) Inventors: Haiyan Wang, Fremont, CA (US);
Hsiu-Khuern Tang, San Jose, CA (US); Abhay Mehta, Austin, TX (US);
Laleh Jalali, San Jose, CA (US);
Maojing Fu, Sunnyvale, CA (US);
Hiroaki Ozaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 358 days.

(21) Appl. No.: 16/127,486

(22) Filed: Sep. 11, 2018

(65) Prior Publication Data
US 2020/0082941 A1    Mar. 12, 2020

(51) Int. Cl.
G16H 50/20 (2018.01)
G06N 20/00 (2019.01)

(52) U.S. Cl.
CPC ............. G16H 50/20 (2018.01); G06N 20/00 (2019.01)

(58) Field of Classification Search
None
See application file for complete search history.

(56) References Cited

U.S. PATENT DOCUMENTS

2002/0087361 A1* 7/2002 Benigno ................ G16H 50/70
                                                        705/3
2012/0065987 A1* 3/2012 Farooq ................. G16H 40/20
                                                        705/2
2012/0150498 A1* 6/2012 Shastri ................... G16H 50/50
                                                        703/2
2013/0185231 A1* 7/2013 Baras ..................... G16H 50/50
                                                        706/12
2013/0197922 A1 8/2013 Vesto
(Continued)

FOREIGN PATENT DOCUMENTS

JP      2016-519807 A    7/2016
WO      2018/073895 A1   6/2019

OTHER PUBLICATIONS

Evelene M Carter, et al., "Predicting length of stay from an electronic patient record system: a primary total knee replacement example", Carter and Potts BMC Medical Informatics and Decision Making 2014, 14:26, p. 1-13.

(Continued)

Primary Examiner — Jonathan Ng
(74) Attorney, Agent, or Firm — Mattingly & Malur, PC

(57) ABSTRACT

In some examples, a system may generate a plurality of care path patient profile models based on a plurality of care path patterns for a plurality of past patient admissions. For example, each care path patient profile model may include a trained classifier. Further, the system may receive information related to a new patient admission, and may generate features from the received information related to the new patient admission. The system may input the features generated from the received information related to the new patient admission into the plurality of care path patient profile models to obtain a respective probability of being classified in a respective care path based on an amount of similarity to the patients who have gone through each care path. In addition, the system may present, on a display, information related to at least one care path pattern in a graphical user interface.

18 Claims, 21 Drawing Sheets

(56) References Cited

U.S. PATENT DOCUMENTS

| | | | |
|---|---|---|---|
| 2014/0279754 A1 | 9/2014 | Barsoum et al. | |
| 2019/0221311 A1* | 7/2019 | Takeuchi | G06N 3/02 |
| 2019/0237200 A1 | 8/2019 | Katsuda | |
| 2020/0243172 A1* | 7/2020 | Brady | G16H 40/20 |

OTHER PUBLICATIONS

Joseph Futoma, et al., "Acomparisonofmodelsforpredictingearlyhospitalreadmissions", Journal of Biomedical Informatics 56 (2015) 229-238.

"Hospital Value-Based Purchasing (VBP) Program", CMS.gov Centers for Medicare & Medicaid Services, Sep. 10, 2018.

"Hospital-Acquired Condition Reduction Program (HACRP)", CMS.gov Centers for Medicare & Medicaid Services, Sep. 10, 2018.

Emanuel Parzen, et al., "Kernel density estimation", Wikipedi A, Sep. 5, 2018.

Ulrike von Luxburg, "A Tutorial on Spectral Clustering", Statistics and Computing, 17 (4), 2007.

Adam Perer, et al., "Mining and exploring care pathways from electronic medical records with visual analytics", Journal of Biomedical Informatics 56 (2015) 369-378.

Readmissions Reduction Program (HRRP), CMS.gov Centers for Medicare & Medicaid Services, Sep. 10, 2018.

Japanese Office Action received in corresponding Japanese Application No. 2019-042605 dated Mar. 31, 2020.

\* cited by examiner

| CARE PATH | LAB TEST(S) | DIAGNOSIS CODE | PROCEDURE CODE | FREQUENCY |
|---|---|---|---|---|
| PATTERN 1 | L:LA4 | D:0388 | P:9672 | 222 |
| PATTERN 2 | L:LA4; LA16 | D:03842 | P:3893 | 241 |
| PATTERN 3 | L:LA4; LA16 | D:0389 | P:9671 | 212 |
| PATTERN 4 | L:LA40; LA62; LA72 | D:0389 | P:9671 | 180 |
| ••• | | | | |

FIG. 2

| Category | Feature |
|---|---|
| Sociodemographic | Age |
| | Sex |
| | Race and/or Ethnicity |
| | Income |
| | Residential census tract in lowest socioeconomic quintile |
| | Employment status |
| | Marital status |
| | Number of people in home |
| | Insurance and/or Medicare/Medicaid status |
| | Education |
| Utilization | Hospitalizations in the past 3, 6, 9, 12 months |
| | ER visits in the past 3, 6, 9, 12 months |
| | Clinic visits in the part 3, 6, 9, 12 months |
| | Missed appointments in the past 3, 6, 9, 12, months |
| | Hospital length of stay history |
| Overall Health and Clinical History | Functional status (ability to perform tasks such as lifting, stooping, walking) |
| | Dependent for activities of daily living (ADLs) |
| | Self-rated quality of life |
| | Cognitive impairment |
| | Visual or hearing impairment |
| | History of mental illness, depression, anxiety |
| | History of alcohol or substance abuse |
| | Admission summary note |
| | Health history: BMI, weight, smoking status, blood pressure, heart rate, temperature, respiratory rate, pain, SpO2 |
| | Comorbidity index |
| | Severity index |
| | Diagnosis Related Group (DRG) history |
| | Lab findings history (number of abnormal results) |
| | Diagnoses history (number and diagnosis categories) |
| | Procedures history (number and procedure categories) |
| | Medications history (number and medication categories) |
| ⋮ | ⋮ |

FIG. 5

| Admission No. | DRG Code | Care Path Pattern | t* | Flow Feature |
|---|---|---|---|---|
| Admission 1 | 7203 | 7203_Pattern 1 | 120 | 1 |
| Admission 2 | 7203 | 7203_Pattern 2 | 120 | 1 |
| Admission 3 | 7203 | 7203_Pattern 47 | 120 | 0 |
| Admission 4 | 0443 | 0443_Pattern 1 | 28 | 1 |
| ... | ... | ... | ... | ... |

FIG. 6

|      | P:1 | P:2 | P:3 | P:4 | P:5 | P:6 | P:7 | P:8 | P:9 | P:10 |
|------|-----|-----|-----|-----|-----|-----|-----|-----|-----|------|
| D:1  | 0   | 1   | 0   | 0   | 0   | 0   | 0   | 1   | 1   | 1    |
| D:2  | 0   | 0   | 0   | 0   | 1   | 0   | 0   | 0   | 0   | 0    |
| D:3  | 0   | 1   | 0   | 0   | 0   | 0   | 0   | 1   | 1   | 1    |
| D:4  | 0   | 0   | 1   | 1   | 1   | 0   | 0   | 0   | 0   | 0    |
| D:5  | 1   | 0   | 0   | 0   | 0   | 1   | 1   | 0   | 0   | 0    |
| D:6  | 0   | 0   | 0   | 0   | 1   | 0   | 0   | 0   | 0   | 0    |
| D:7  | 0   | 0   | 1   | 1   | 0   | 0   | 0   | 0   | 0   | 0    |
| D:8  | 0   | 1   | 0   | 0   | 0   | 0   | 1   | 1   | 1   | 1    |
| D:9  | 1   | 0   | 0   | 0   | 0   | 1   | 0   | 0   | 0   | 0    |
| D:10 | 0   | 0   | 0   | 0   | 0   | 1   | 0   | 0   | 0   | 0    |

FIG. 8

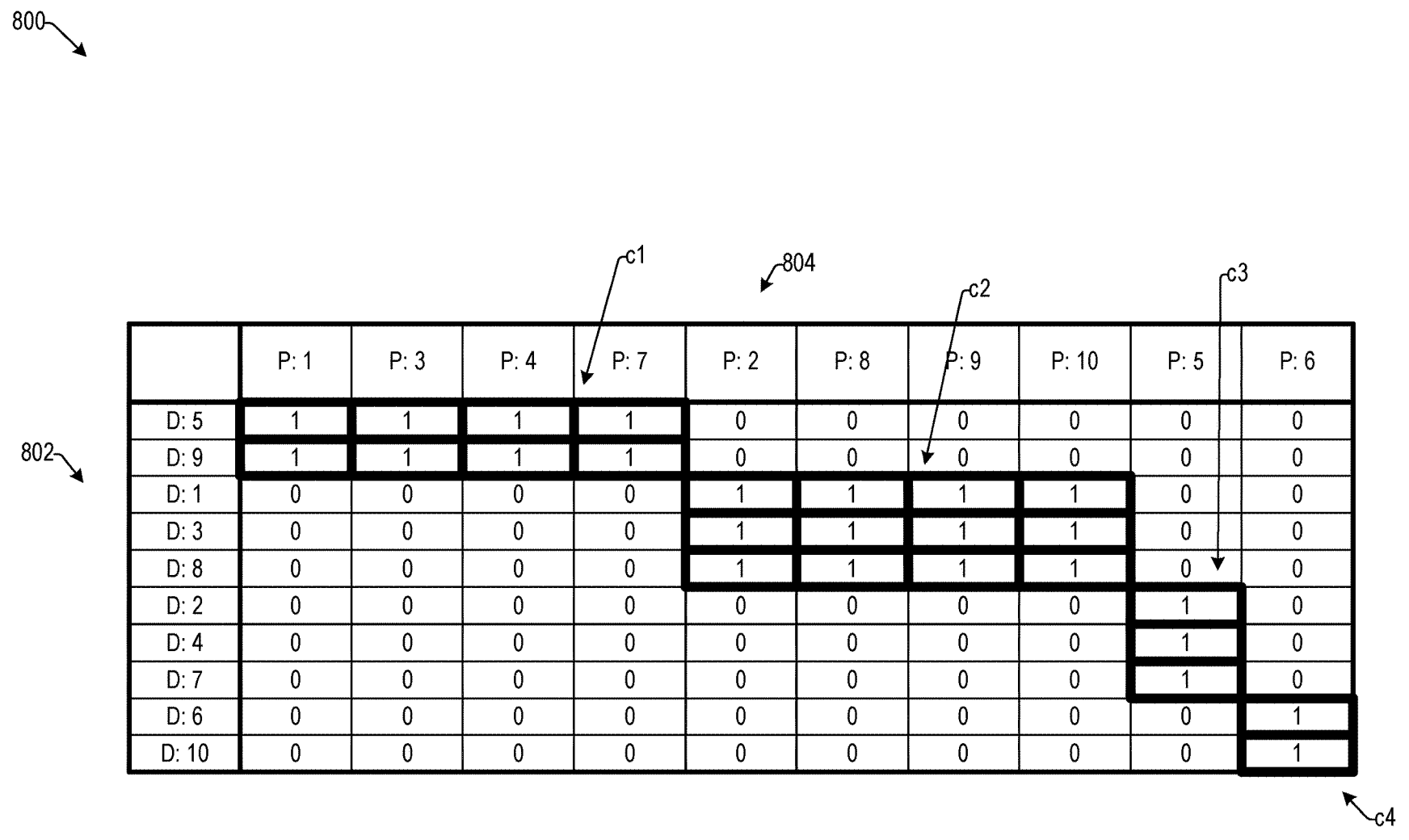

| | P:1 | P:3 | P:4 | P:7 | P:2 | P:8 | P:9 | P:10 | P:5 | P:6 |
|---|---|---|---|---|---|---|---|---|---|---|
| D:5 | 1 | 1 | 1 | 1 | 0 | 0 | 0 | 0 | 0 | 0 |
| D:9 | 1 | 1 | 1 | 1 | 0 | 0 | 0 | 0 | 0 | 0 |
| D:1 | 0 | 0 | 0 | 0 | 1 | 1 | 1 | 1 | 0 | 0 |
| D:3 | 0 | 0 | 0 | 0 | 1 | 1 | 1 | 1 | 0 | 0 |
| D:8 | 0 | 0 | 0 | 0 | 1 | 1 | 1 | 1 | 0 | 0 |
| D:2 | 0 | 0 | 0 | 0 | 0 | 0 | 0 | 0 | 1 | 0 |
| D:4 | 0 | 0 | 0 | 0 | 0 | 0 | 0 | 0 | 1 | 0 |
| D:7 | 0 | 0 | 0 | 0 | 0 | 0 | 0 | 0 | 1 | 0 |
| D:6 | 0 | 0 | 0 | 0 | 0 | 0 | 0 | 0 | 0 | 1 |
| D:10 | 0 | 0 | 0 | 0 | 0 | 0 | 0 | 0 | 0 | 1 |

FIG. 10

| Admission No. | Feature: Diagnosis_Procedure_c1 | Feature: Diagnosis_Procedure_c2 | Feature: Diagnosis_Procedure_c3 | Feature: Diagnosis_Procedure_c4 |
|---|---|---|---|---|
| Admission 1 | 1 | 0 | 0 | 0 |
| Admission 2 | 1 | 0 | 0 | 0 |
| Admission 3 | 0 | 1 | 0 | 0 |
| Admission 4 | 0 | 0 | 0 | 1 |
| ••• | ••• | ••• | ••• | ••• |

FIG. 12

CARE PATH ANALYSIS AND MANAGEMENT PLATFORM

BACKGROUND

Care paths, also referred to as clinical pathways, are used to manage quality in healthcare by providing standardization to care processes. A single care path may refer to multiple clinical guidelines on several topics for a specific group of patients, in which various optimized interventions by the professionals involved are defined based on evidence. The use of care paths for treatment of patients has been shown to reduce variability in clinical practice and generally improve the outcomes for the patients. For example, care paths may be used to standardize care management and to improve clinical processes by reducing risks, duplication, and variation in treatment of patients.

For each individual patient, a properly conceived care path may provide a synergy between a number of different specialties and caring functions, and may include foreseeable actions that are likely to be best practices for patients "similar" to this particular patient. However, due to the large number of possible variables for treatment of individuals, determining the most effective care path is challenging. The use of care paths may optimize outcomes in a variety of settings such as acute care and home care, and can help reduce incidences of hospital readmissions, patient relapses, or the like. Further, the use of care paths may improve the efficiency of patient care through managing various expensive healthcare resources.

SUMMARY

Some implementations include arrangements and techniques in which a system may generate a plurality of care path patient profile models based on a plurality of care path patterns for a plurality of past patient admissions. For example, each care path patient profile model may include a trained classifier. Further, the system may receive information related to a new patient admission, and may generate features from the received information related to the new patient admission. The system may input the features generated from the received information related to the new patient admission into the plurality of care path patient profile models to obtain a respective probability of being classified in a respective care path based on an amount of similarity to the patients who have gone through each care path. In addition, the system may present, on a display, information related to at least one care path pattern in a graphical user interface (GUI).

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 2 illustrates an example data structure of mined care path patterns for a group of patients according to some implementations.

FIG. 5 illustrates an example data structure of example features according to some implementations.

FIG. 6 illustrates an example data structure of example admissions with generated features according to some implementations.

FIG. 8 illustrates an example data structure of an incidence matrix including transitions from diagnosis to procedures according to some implementations.

FIG. 10 illustrates an example data structure of the incidence matrix of FIG. 8 after bi-clustering according to some implementations.

FIG. 12 illustrates an example data structure of admissions with features generated using bi-clustering according to some implementations.

DETAILED DESCRIPTION

Figure 1:
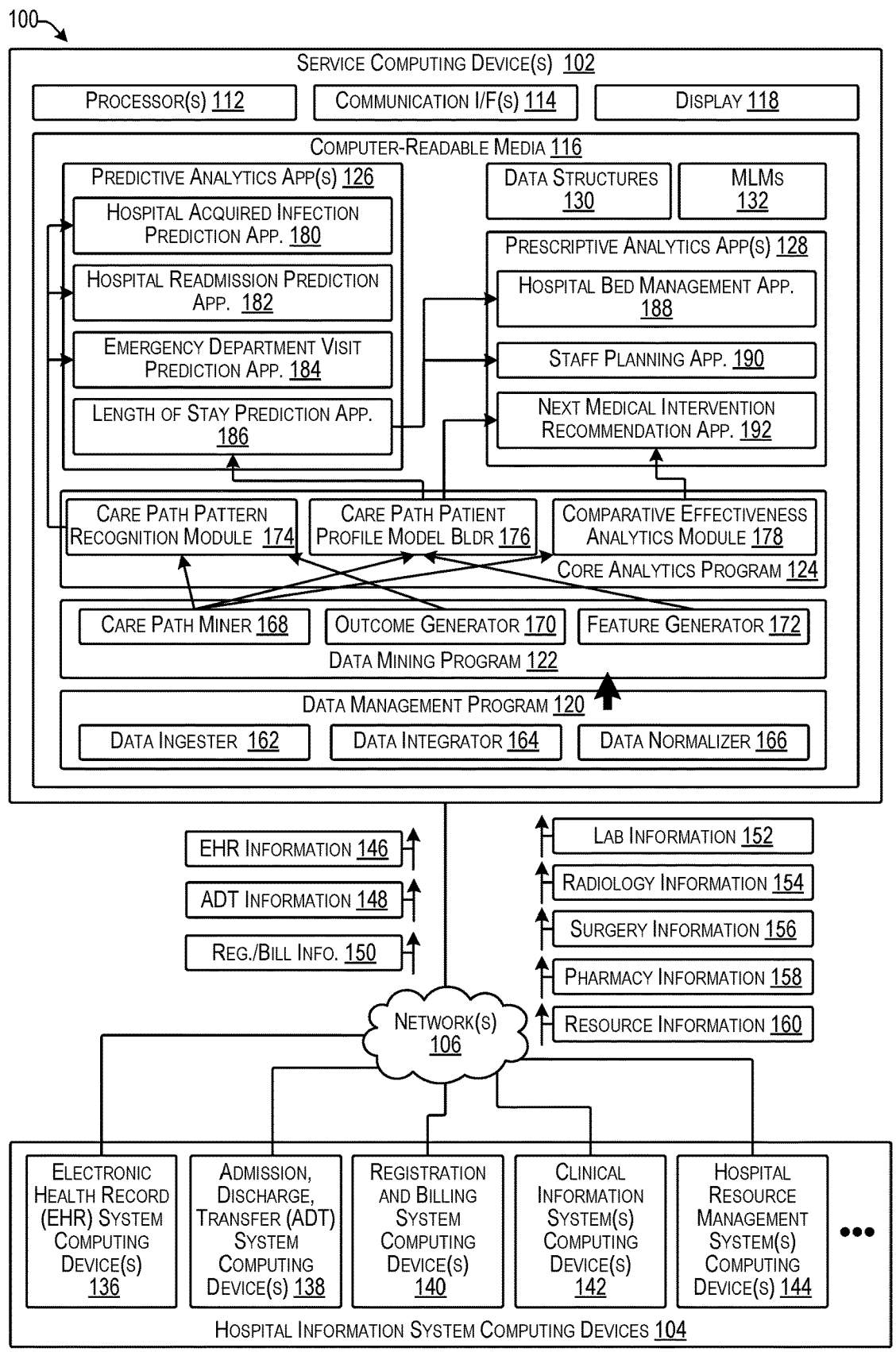
FIG. 1 illustrates an example architecture of a system for performing care path analytics and managing resources according to some implementations.

Some implementations herein are directed to techniques and arrangements for a care path analytics platform that provides analytics applications for determining care paths, predicting patient risk, and managing associated resources. For example, care paths may be analyzed at population level using data mining and machine learning techniques to discover inherent patterns within the care paths. In addition, the techniques herein enable the users to determine and visualize the associations of individual care paths with various risks, such as hospital readmissions, hospital-acquired conditions, likely length of stay in the hospital, likelihood of mortality, and so forth. Accordingly, implementations herein are able to solve a problem of matching newly admitted patients with an optimal care path for that patient based on using machine learning to determine respective probabilities of the patient being classified as being similar to the patients who have gone through each care path. For example, the higher the probability, the more likely the patient will have a similar outcome to patients who have gone through a particular care path. Furthermore, through use of a GUI able to provide a comparative visualization of one or more care paths and associated outcomes, medical professionals are able to use the system herein for making an educated and comprehensive determination of an optimal care path for each new patient.

The care path analytics platform may include one or more programs for determining care paths and enabling a plurality of predictive and prescriptive analytics applications, such as a data management program, a data mining program, and a core analytics program, and that provide information to the analytics applications. For instance, the data management program may receive and integrate data from a plurality of different health information systems, and further, may perform data pre-processing, normalization, and the like, on the received data.

The data mining program may apply frequent-pattern mining techniques to care path data for determining care paths based on frequency and for generating features from individual data sources. In addition, the data mining program may summarize care outcomes of interest, such as hospital readmissions, hospital-acquired conditions (HACs), and hospital length of stay (LOS). The core analytics program may include care path pattern recognition module, a care path patient profile model builder, and care path comparative effectiveness analysis logic.

The core analytics program may interact with a predictive analytics application and/or a prescriptive analytics application. For example, the predictive analytics application may include a hospital acquired infection prediction application, a hospital readmission prediction application, an emergency department visit prediction application, and/or a length of stay prediction application. In addition, the prescriptive analytics application may include hospital bed management logic, staff planning logic, and next medical intervention recommendation logic. Each of these functions are described in additional detail below.

Furthermore, some examples herein provide a plurality of techniques for executing critical analytics applications on the care path analytics platform. Accordingly, the care path analytics platform herein may provide a holistic view of interventions experienced by patients and may enable a variety of analytics applications to turn otherwise isolated data into actions for determining suitable care paths for patients. For example, the platform may analyze the care path patterns that are highly correlated with an outcome of interest, such as readmission. Further, the care path analytics platform may employ data mining and machine learning based analytics to mitigate patient risk and improve operations of hospitals or other health care organizations by analyzing patterns across a number of different data sources, building care path patient profile models, recommending next intervention actions, and the like.

In some examples, the care path analytics platform may integrate data from a plurality of diverse health information systems, such as an electronic health record (EHR) system, an admission, discharge, transfer (ADT) system, a registration and billing system, a clinical information system, a hospital resource management system, or the like. The data integration process may be analytics oriented. In addition, the analytics applications supported by the care path analytics platform may include, but are not limited to, hospital-acquired infection risk prediction, hospital readmission risk prediction, emergency department visit prediction, length of stay (LOS) prediction, next medical intervention recommendation, hospital bed management, and staff planning.

In some implementations, the system may generate a plurality of care path patient profile models based on a plurality of care path patterns for a plurality of past patient admissions. For example, each care path patient profile model may include a trained classifier that represents the main characteristics of the patients who have gone through the care path. Further, the system may gather and analyze information related to a new patient admission and may generate features from the gathered information related to the new patient admission. The system may input the features generated from the gathered information related to the new patient admission into the plurality of care path patient profile models to obtain a respective probability of being similar to the patients who have gone through each care path. The system may use the generated probabilities to determine the best possible next interventions for the new patient admission. In addition, the system may analyze the patterns and risks among a plurality of care paths, and may input the analyzed patterns to a plurality of prediction models to help reduce patient risks and predict patient length of stay. The system may input the predicted length of stay to a healthcare resource management system for use in managing healthcare resources. Further, the system may present information related to at least one care path pattern in a graphical user interface (GUI) on a display.

The platform and system described herein may be used as a standalone solution or may be integrated with existing systems that provide other functionalities for hospital care management and operations management. For discussion purposes, some example implementations are described in the environment of one or more computing devices that determine suitable care paths for patients and provide corresponding visualizations in a user interface. However, implementations herein are not limited to the specific examples provided, and may be extended to other types of data analysis techniques, other types of health care environments, other system architectures, other graphics effects, and so forth, as will be apparent to those of skill in the art in light of the disclosure herein.

FIG. 1 illustrates an example architecture of a system 100 for performing care path analytics and managing resources according to some implementations. The system 100 includes at least one service computing device 102 that is able to communicate with one or more hospital information system computing devices 104, such as through one or more networks 106. In some examples, the service computing device(s) 102 and/or hospital information system computing device(s) 104 may include one or more servers, personal computers, or other types of computing devices that may be embodied in any number of ways. For example, in the case of a personal computer, the programs, other functional components, and at least a portion of data storage may be implemented on the personal computer and/or may be partially implemented at a network location, such as through cloud-based storage, cloud-based processing, or the like. Alternatively, in the case of a server, the programs, other functional components, and at least a portion of data storage may be implemented on at least one server, such as a stand-alone server, or one or more servers in a cluster of servers, a server farm or data center, a cloud-hosted computing service, and so forth, although other computer architectures may additionally or alternatively be used.

In the illustrated example, the service computing device 102 includes, or may have associated therewith, one or more processors 112, one or more communication interfaces (I/Fs) 114, one or more computer-readable media 116, and a display 118. Each processor 112 may be a single processing unit or a number of processing units, and may include single or multiple computing units, or multiple processing cores. The processor(s) 112 can be implemented as one or more central processing units, microprocessors, microcomputers, microcontrollers, digital signal processors, state machines, logic circuitries, graphics processing units, systems on chips, and/or any devices that manipulate signals based on operational instructions. For instance, the processor(s) 112 may be one or more hardware processors and/or logic circuits of any suitable type specifically programmed or configured to execute the algorithms and processes described herein. The processor(s) 112 may be configured to fetch and execute computer-readable instructions stored in the computer-readable media 116, which can program the processor(s) 112 to perform the functions described herein.

The computer-readable media 116 may include volatile and nonvolatile memory and/or removable and non-removable media implemented in any type of technology for storage of information such as computer-readable instructions, data structures, program modules, or other data. For example, the computer-readable media 116 may include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the service computing device 102, the computer-readable media 116 may be a tangible non-transitory medium to the extent that, when mentioned, non-transitory computer-readable media exclude media such as energy, carrier signals, electromagnetic waves, and/or signals per se. In some cases, the computer-readable media 116 may be at the same location as the service computing device(s) 102, while in other examples, the computer-readable media 116 may be partially remote from the service computing device(s) 102.

The computer-readable media 116 may be used to store any number of functional components that are executable by the processor(s) 112. In many implementations, these functional components comprise instructions or programs that are executable by the processor(s) 112 and that, when executed, specifically program the processor(s) 112 to perform the actions attributed herein to the service computing device 102. Functional components stored in the computer-readable media 116 may include a data management program 120, a data mining program 122, a core analytics program 124, one or more predictive analytics applications 126 and one or more prescriptive analytics applications 128, each of which is described additionally below.

Additional functional components maintained in the computer-readable media 116 of the service computing device(s) 102 may include an operating system (not shown in FIG. 1) that may control and manage various functions of the service computing device(s) 102. In some cases, the functional components may be stored in a storage portion of the computer-readable media 116, loaded into a local memory portion of the computer-readable media 116, and executed by the one or more processors 112. Numerous other software and/or hardware configurations will be apparent to those of skill in the art having the benefit of the disclosure herein.

In addition, the computer-readable media 116 may store data, which may include a plurality of data structures 130 used for performing the functions and services described herein. For example, the computer-readable media 116 may store data received from the hospital information system computing devices 104, may store tables, databases, heat maps, and other data structures, such as may be generated from the received data. In addition, the computer readable media 116 may store one or more machine learning models 132 that may be generated and trained using the received data and the data structures 130. Additional description of the data structures 130 and machine learning models 132 is included below.

The service computing device 102 may also include or maintain other functional components and data, which may include programs, drivers, etc., and other data used or generated by the functional components. Further, the service computing device 102 may include many other logical, programmatic, and physical components, of which those described above are merely examples that are related to the discussion herein.

The service computing device 102 may further include or may otherwise be in communication with the display 118 for presenting a graphic user interface (GUI) (not shown in FIG. 1) including a care path visualization, one or more selected care paths, and the predicted risk profiles for the selected care paths, as discussed additionally below. A medical professional or other user may execute and interact with the GUI on the display 118 for determining an optimal care path for a selected patient and a selected medical facility, such as a hospital or other health care organization.

Additionally, in some examples, a first portion of the operations described herein may be performed by a first one of the service computing devices 102, and another portion of the operations may be performed by a second one of the service computing devices 102. As one example, one or more first service computing devices 102 may execute the data management program 120, the data mining program 122, and the core analytics program 124, while one or more second service computing devices 102 may execute the predictive analytics application(s) 126 and the prescriptive analytics application(s) 128. Alternatively, of course, in other examples, a single service computing device 102 may be employed. Numerous other variations will be apparent to those of skill in the art having the benefit of the disclosure herein.

The communication interface(s) 114 may include one or more interfaces and hardware components for enabling communication with various other devices, such as over the one or more networks 106. Thus, the communication interfaces 114 may include, or may couple to, one or more ports that provide connection to the network(s) 106 for communicating with the hospital information system computing device(s) 104. For example, the communication interface(s) 114 may enable communication through one or more of a LAN (local area network), WAN (wide area network), the Internet, cable networks, cellular networks, wireless networks (e.g., Wi-Fi) and wired networks (e.g., fiber optic, Ethernet, Fibre Channel,), direct connections, as well as close-range communications, such as BLUETOOTH®, and the like, as additionally enumerated below.

The one or more networks 106 may include any type of network, including a LAN, such as an intranet; a WAN, such as the Internet; a wireless network, such as a cellular network; a local wireless network, such as Wi-Fi; short-range wireless communications, such as BLUETOOTH®; a wired network including fiber optics, Ethernet, Fibre Channel, or any other such network, a direct wired connection, or any combination thereof. Accordingly, the one or more networks 106 may include both wired and/or wireless communication technologies. Components used for such communications can depend at least in part upon the type of network, the environment selected, or both. Protocols for communicating over such networks are well known and will not be discussed herein in detail. Accordingly, the service computing device(s) 102 and the hospital information system computing device(s) 104 are able to communicate over the one or more networks 106 using wired or wireless connections, and combinations thereof.

In some examples, the hospital information system computing device(s) 104 may have a hardware configuration (not shown in FIG. 1) similar to the service computing device(s) 102 discussed above. For example, the hospital information system computing device(s) 104 may include any of the examples of processors 112 discussed above, any of the examples of communication interfaces 114 discussed above, and any of the examples of computer-readable media 116 discussed above.

The hospital information system computing device(s) 104 may include computing devices of various different hospital information systems, several examples of which are shown in FIG. 1. Thus, in the illustrated example, the hospital information system computing device(s) 104 include one or more electronic health record (EHR) computing devices 136, one or more admission, discharge, transfer (ADT) system computing devices 138, one or more registration and billing system computing devices 140, one or more clinical information system computing devices 142, one or more hospital resource management system computing devices 144, and so forth.

The hospital information system computing devices 104 may send various types of data to the data management program 120 executing on the service computing device(s) 102. Examples of data that may be received by the data management program 120 include EHR information 146, such as detailed patient data for individual patients, that may be provided by the electronic health record system computing device 136; ADT information 148 that may be provided by the admission, discharge, transfer system computing device 138 related to patient admissions and discharges from hospitals or the like; registration and billing information 150 that may be provided by the registration and billing system computing device 140; clinical information, such as lab information 152, radiology information 154, surgery information 156, and pharmacy information 158, for individual patients that may be provided by the clinical information system computing devices 142; and resource information 160 regarding various hospital resources that may be provided by the hospital resource management system computing device 144.

The data management program 120 receives the data 146-160 from multiple health information system computing devices 104 that are employed by a healthcare organization. As discussed below, the received data may include any information that may be used to derive candidate predictors, referred to as features, that may be used by the analytics applications 126 and/or 128. The data management program 120 may include a data ingester 162, which may be a program module of the data management program 120 that may receive the data 146-160 from the hospital information system computing devices 104 and may store the received data in one or more of the data structures 130.

In addition, the data management program 120 may include a data integrator 164, which may be a program module of the data management program 120 that integrates the data received from the various different health information system computing devices to enable use of the data together, regardless of the source. For instance, the data integrator 164 may integrate data from a plurality of diverse health information systems. As one example, data from different sources may need to be joined, merged, correlated, or otherwise integrated together before the data is conveniently useable in the data mining process. In some examples, the data integration process may be analytics oriented, as discussed additionally below.

In addition, the data management program 120 may include a data normalizer 166, which may be a program module of the data management program 120 that may normalize the received data into various uniform formats, or the like, depending on the data type, to enable further use of the data by the data mining program 122. For example, data standardization, cleansing, and other types of data normalization may be employed, which may address differences in data formats, or the like, such as due to the evolution of EHR system within the organization, human factors (e.g., different people may enter the same type of data slightly differently), and the like. For example, different diagnosis-related group (DRG) codes such as MS-DRG (Medicare-severity DRG) or APR-DRG (all-patient-refined DRG) may be used. For instance, it may be common to have both International Classification of Diseases-9 (ICD-9) and ICD-10 codes used for diagnoses and procedures in the same health organization, such as the same hospital, or the like. Furthermore, different units may be used for the same types of lab test results in some cases. In these situations, data standardization and normalization is performed to ensure accuracy before any knowledge and insight is extracted from the data. Accordingly, the data normalizer 166 may automatically normalize the data from various sources into a normalized (e.g., specified) format, which may have been specified in advance for the particular data type.

The data mining program 122 may digest the integrated and normalized data stored by the data management program 120. For example, the data mining program 122 may perform foundational data mining tasks that serve as the base of the core analytics performed by the core analytics program 124. The data mining program may include three subprograms (also referred to as program modules), namely a care path miner 168, an outcome generator 170 and a feature generator 172.

The data mining program 122 may execute the care path miner 168 to access the received data in the data structures 130. The care path miner 168 may apply frequent sequential pattern mining techniques to the integrated and normalized data in the data structures 130 to determine sequences of clinical interventions received by a group of patients. For example, a selected group of patients may be a plurality of patients with the same DRG code or who are otherwise defined by the same classification criteria, e.g., by having one or more specified characteristics in common. Accordingly, a selected group of patients may be configurable based on one or more user-defined criteria or based on one or more default criteria.

The inherent large variations in healthcare data pose modeling and computational challenges for mining data related to care path patterns. For example, there are thousands of lab tests, diagnosis codes, procedure codes, types of drugs, and so forth. Further, even for the same type of intervention event, patients may experience different durations and outcomes.

The care path miner 168 may be configured to mine data to form a foundation for the analytics applications 126, which enable actions such as next treatment recommendation, risk prediction and prevention, and the like. One issue with the large amount of variation in healthcare data is that it results in a large number of patterns associated with only a few instances if each event is recorded with its corresponding duration. To overcome this issue, the care path miner 168 may model the care path as a sequence of lab→diagnosis→procedure, which covers the major interventions that patients experience during their stay with a hospital. The sequence of lab→diagnosis→procedure may be referred to as a "flow" while sub-sequences, such as lab→diagnosis, or diagnosis→procedure, may be referred to as "transitions". FIG. 2 discussed below illustrates an example of mined care path patterns for a group of patients with the same DRG code determined by the care path miner 168.

Figure 3:
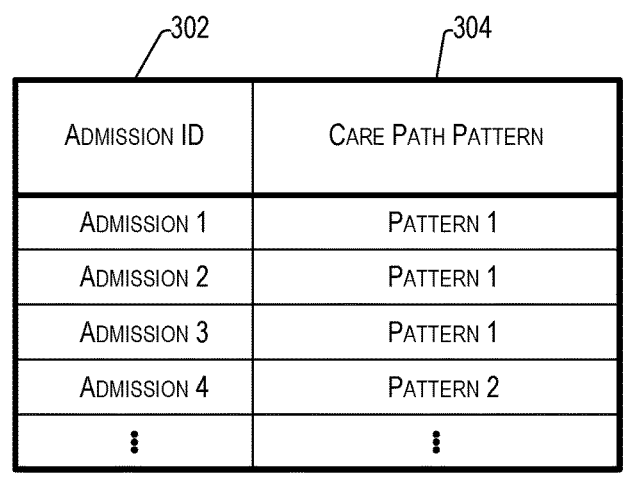
FIG. 3 illustrates an example data structure of admission and care path associations according to some implementations.

In addition, the care path miner 168 may be configured to determine the association between admissions and the care path patterns and store this information to another data structure. FIG. 3 discussed below illustrates an example data structure including the association between admission and care paths.

The outcome generator 170 may execute an outcome-based care path pattern analysis that may be used by the analytics applications 126 and/or 128. For example, the outcome generator 170 of the data mining program 122 may be executed to determine the analysis targets. The analysis targets may be referred to as analytics outcomes. Examples of the outcomes may include hospital-acquired infection that may be used for hospital-acquired infection prediction; patient readmissions within a period (e.g., 30 days, 60 days, etc.) that may be used for hospital readmission risk prediction; and length of stay that may be used for LOS prediction.

Figure 4:
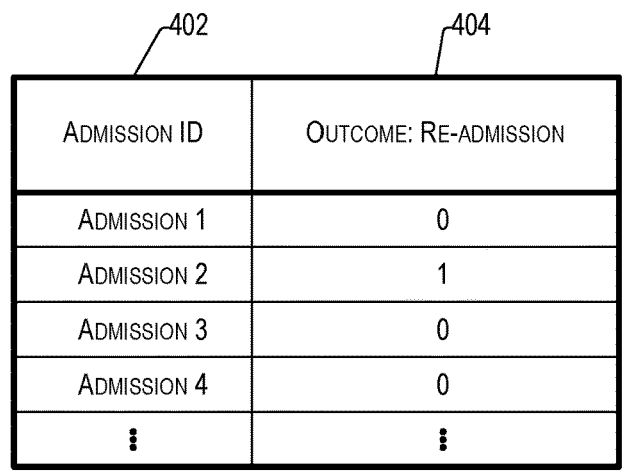
FIG. 4 illustrates an example data structure of outcomes that result in readmission according to some implementations.

Some examples herein may use a binary variable to represent hospital-acquired infection and readmission. That is, for each admission, if a patient acquired a type of infection of interest during the stay, the corresponding outcome variable for this admission is 1, otherwise, 0. Similarly, for each admission, if a patient was readmitted to the hospital within a pre-defined period after the discharge, the corresponding outcome variable for this admission is 1, otherwise, 0. FIG. 4 illustrates an example of an outcome data structure for readmission, as discussed additionally below. In addition, the length of stay may be calculated as the difference between discharge date and admission date, and the outcome variable may be denoted as Y. For K admissions under analysis, Y may be a vector of length of K.

In addition, the data mining program 122 includes the feature generator 172, which extracts features from the mined data. For example, the core analytics program may use extracted features to build care path patient profile models. The care path patient profile may include a set of patient characteristics plus the interactions among the characteristics that are distinctive for each care path pattern. The patient characteristics may include patient demographic information, genetic information, health history, clinical history, and so forth. At least some of the patient characteristics may be used as features for generating and training care path patient profile models. With the care path patient profile, rather than using some simple ad-hoc criteria based on gender and age, say, the core analytics program may more accurately determine which care path a newly admitted patient may be most likely to experience. This may not only help the medical professionals decide the next intervention, but may also assist the hospital to manage the hospital resources such as beds, staff, equipment, and other resources. The care path patient profile models may be generated and trained as machine learning models based on determined features. Additional details of generating the care path patient profile models are discussed below with respect to the core analytics program 124.

To facilitate building a care path patient profile model by the core analytics program 124, the feature generator 172 of the data mining program 122 may generate the potential patient characteristics, i.e., features, at each admission level. The feature generator 172 may generate features mainly from each individual data source, e.g., the EHR system, the ADT system, clinical information systems, etc. These may be referred to as basic features. FIG. 5 discussed below illustrates an example data structure including potential features generated by the feature generator 172 of the data mining program 122. The information in FIG. 5 is information that may be obtained during or may be otherwise associated with each admission of a patient as discussed herein. Additional information that may be associated with each admission may include a time and date of the admission and a DRG code associated with each admission.

Cross-data-source features such as care path related features may be generated by a care path pattern recognition module 174 included in the core analytics program 124. The features generated by care path pattern recognition module 174 may also be used by the predictive analytics applications 126.

The core analytics program 124 may include analytics components that support the analytics applications 126 and 128. Core analytics program 124 may include the care path pattern recognition module 174 that may be used for prediction; a care path patient profile model builder; and a care path comparative effectiveness analytics module 178. The care path pattern recognition module 174 may be executed to determine a pattern of mined care paths and to use the determined pattern for the predictive analytics application(s) 126. For instance, the care path pattern recognition module 174 may be used by a hospital-acquired infection risk prediction application 180, a hospital readmission risk prediction application 182, an emergency department visit prediction application 184, and/or a length of stay (LOS) prediction application 186, each of which is discussed additionally below.

In some examples, the mined care paths may be treated as categorical variables for predicting the target of interest (e.g., hospital-acquired infection, hospital readmission, emergency department visit, etc.). Implementations herein include two methods to generate features that are useful for predictive analytics application(s) 126 based on mined care path patterns. For instance, the care path pattern recognition module may generate two categories of features, a first category being binary and a second category being multi-class. In terms of sequence granularity, the generated features may be related with the whole flow as well as each transition of the care paths. For binary features, the care path pattern recognition module 174 may cluster the care path based on the frequency of care path. For multi-class categorical features, the care path pattern recognition module 174 may apply a bi-clustering technique to cluster care paths into groups.

For binary features, the care path pattern recognition module 174 may cluster the care path based on the frequency of care path by clustering the care paths into frequent care paths and infrequent care paths. In some cases, these may correspond to normal care paths and special care paths. If the number of admissions associated with a particular care path pattern exceeds a threshold number, then that care path pattern may be classified as frequent; otherwise, that care path pattern is classified as infrequent. For various different groups of patients, such as based on different DRGs, the threshold number may be different since the number of admissions for different groups of patients may vary substantially. To determine the appropriate threshold for each group of patients, some implementations herein may use a heuristic based on mutual information between the potential feature and the prediction target of interest y, e.g., a re-admission label.

As one example, suppose that, for a selected group of patients, there are K total admissions and the K admissions went through n different care path patterns, denoted by $p_1$, $p_2$, $p_3$, ..., $p_n$, with the corresponding frequency $f_1$, $f_2$, $f_3$, ..., $f_n$. An example data structure of some mined path patterns is described below with respect to FIG. 2. In addition, for a frequency number threshold t, if $f_i \geq t$, then the corresponding care path pattern $p_i$ is treated as frequent. If $f_i < t$, then the corresponding pattern $p_i$ is treated as infrequent. The set of frequent patterns may be denoted as F, while the set of infrequent patterns may be denoted as $F^c$. For a selected admission of interest k, suppose the selected admission underwent care path pattern $p_j$. If $p_j \in F$, then assign 1 to this admission, denoted by $x_k = 1$. Otherwise, $x_k = 0$. Further, denote $X(t) = \{x_1, x_2, ..., x_K\}$ as the binary vector generated when the frequency number threshold is set at t. For these K admissions, the corresponding prediction target, e.g., re-admission label in this example, is $Y = \{y_1, y_2, ..., y_K\}$. In addition, the mutual information between $X(t)$ and Y may be denoted as $I(Y, X(t))$. To get the most information, the care path pattern recognition module 174 may choose a threshold t* such that $t^* = \mathrm{argmax}(I(Y, X(t)))$.

Mutual information is a well-known concept; for the two binary vectors Y and X(t), their mutual information equals $$\sum_{i,j} (n_{ij}/K) \log(K n_{ij} / n_i n_{.j}),$$

where $n_{ij}$ is the number of pairs $(x_k, y_k)$ that equals (i, j), for i=0, 1 and j=0, 1, and $n_{i.} = n_{i0} + n_{i1}$; $n_{.j} = n_{0j} + n_{1j}$. Since X(t) depends on t, so does the mutual information, and the threshold t* that maximizes the mutual information may be chosen by enumerating all the possible values of X(t) along with their corresponding mutual information with Y. In this example, there are n frequencies $f_1$, $f_2$, $f_3$, ..., $f_n$, and the possible values of X(t) are obtained by setting t equal to each $f_i$ in turn.

Furthermore, for a different group of patients, such as a group of patients having different DRG codes, t* may be different. The features generated for a group of index admissions may be added to a data structure, such as is described with respect to FIG. 6 below. In addition, an example process for generating the features through clustering based on care path frequencies is described below with respect to FIG. 7.

Figure 7:
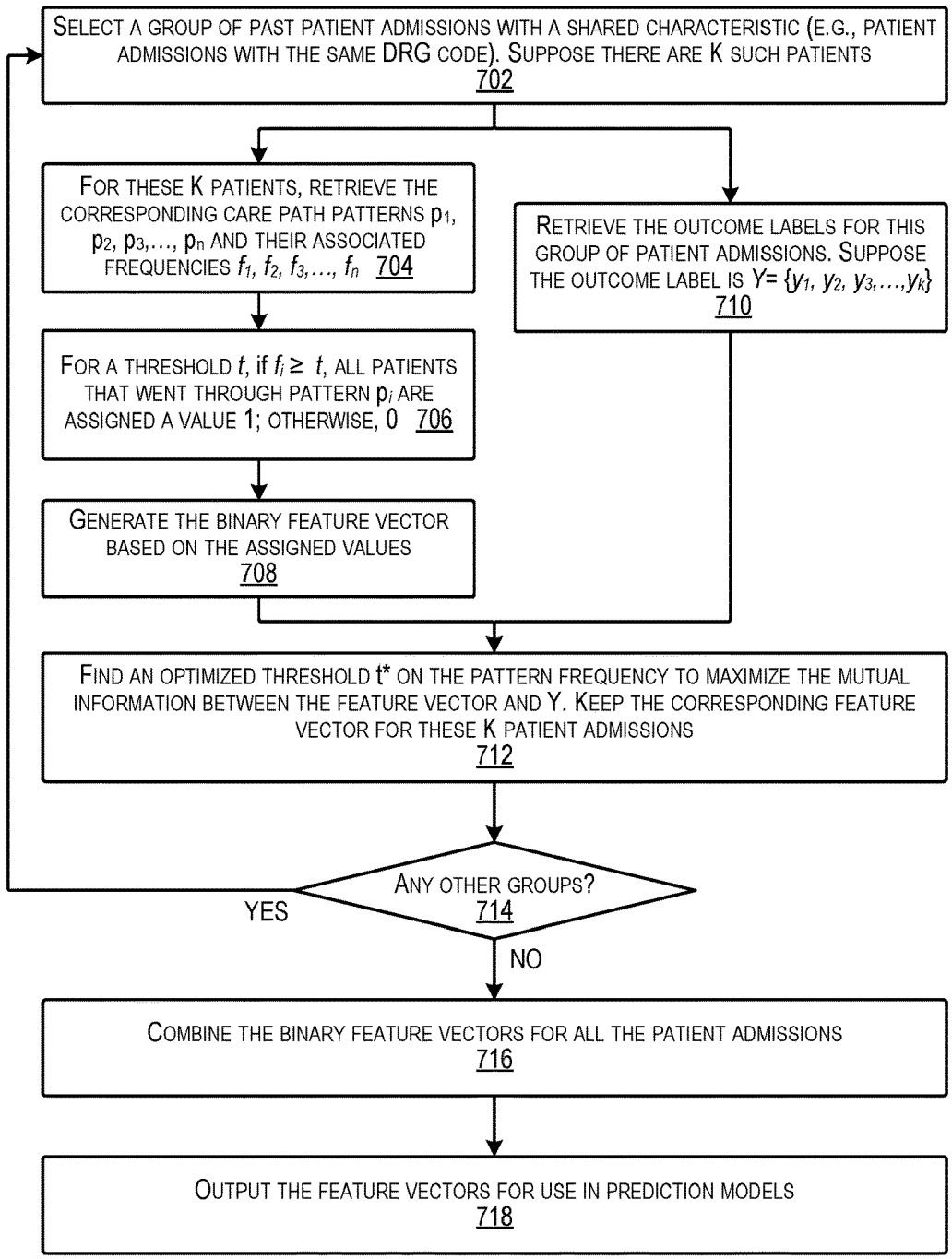
FIG. 7 is a flow diagram illustrating an example process for clustering care paths based on frequency according to some implementations.

The above process, as also discussed with respect to FIG. 7, considers the frequency of the whole flow of a care path. In other examples herein, the information regarding the prediction target may be in each transition, e.g., lab→diagnosis and diagnosis→procedure. Accordingly, binary features may be created based on each transition as well. A process similar to that described above and with respect to FIG. 7 for generating whole flow based features can be applied for generating features from the transitions. For example, care path pattern recognition module 174 may first consider all the patterns for each transition lab→diagnosis and diagnosis→procedure, separately, for a group of patients. For each transition, the care path pattern recognition module 174 may determine the optimal threshold based on the mutual information. Next, the care path pattern recognition module 174 may apply the optimal threshold to generate a binary feature for each admission.

In some cases, binary features may be too rudimentary and not sufficiently discriminative for producing a desired level of accuracy. Accordingly, implementations herein may apply an alternative method for generating more granular features by applying a bi-clustering technique. Bi-clustering, also called co-clustering, two-mode clustering, or block clustering, clusters two dimensions simultaneously. For example, bi-clustering may enable concurrent clustering of both the rows and the columns of a matrix. As one example, given a set of m different lab tests and n different diagnoses, the number of patient admissions that have gone through each pair of a particular lab test and a particular diagnosis forms an m×n matrix. The bi-clustering algorithm may rearrange rows and columns of the m×n matrix so that a subset of lab tests (rows) may be highly associated with a subset of diagnoses (columns), but not highly associated with other diagnoses (columns). That is, for patients who have experienced a certain subset of lab tests may also receive a certain subset of diagnoses, but rarely receive other diagnoses. Thus, a bi-clustering algorithm may look for patterns by analyzing two variables at the same time. Various different bi-clustering algorithms may be applied in the examples herein, such as spectral clustering, block clustering, interrelated two-way clustering, and so forth.

As one example, the care path pattern recognition module 174 may consider each transition in a care path, i.e., lab test→diagnosis, diagnosis→procedure. That is, the two dimensions that are analyzed simultaneously are either 1) lab test→diagnosis or 2) diagnosis→procedure. Although there may be a large amount of different lab tests, diagnosis codes and procedure codes associated with a group of patients, some transitions may be deemed to be "similar" to each other. The similarity may be measured in terms of three options: a) the co-occurrence of the two elements in transitions; b) the frequency of transitions; and/or c) the response rate of transitions.

For option a), the care path pattern recognition module 174 may use an incidence matrix to represent the co-occurrence of the two elements in a transition (i.e., a lab test and a diagnosis code or a diagnosis code and a procedure code). In an incidence matrix, rows and columns represent the two dimensions of a transition. A cell may have value of 1 if the transition from the corresponding row and the corresponding column appears in the data. Otherwise, the cell may have a value of 0.

For option b), the care path pattern recognition module 174 may use a transition frequency matrix. To obtain a transition frequency matrix, each cell in the incidence matrix may be replaced by the number of admissions that have gone through the corresponding transition.

For option c), the care path pattern recognition module 174 may use a transition response rate matrix. If the prediction target is of binary feature, e.g., readmission risk, the response rate may be defined as the percentage of admissions that have positive outcomes (e.g., readmitted) for a group of admissions that have the same transition. If the prediction target is the length of stay (LOS), the response rate may be defined as the average length of stay for that group. To generate a response rate matrix, each cell in the incidence matrix may be replaced by the response rate of the admissions that have gone through the corresponding transition.

The care path pattern recognition module 174 may apply bi-clustering techniques to these matrices to cluster the transitions in the care paths into blocks such that the transitions within a block are deemed to be "similar", while the transitions across different blocks may exhibit significant variations. Each block may represent a new category, e.g., a new feature.

As discussed additionally below, FIG. 8 illustrates an example incidence matrix in which the rows represent diagnosis codes and the columns represent procedure codes for a group of patients. In addition, the care path pattern recognition module 174 may generate a heat map to provide a visualization of this incidence matrix, such as for presentation in a user interface on the display 118. An example of the heat map is described below with respect to FIG. 9.

Figure 11:
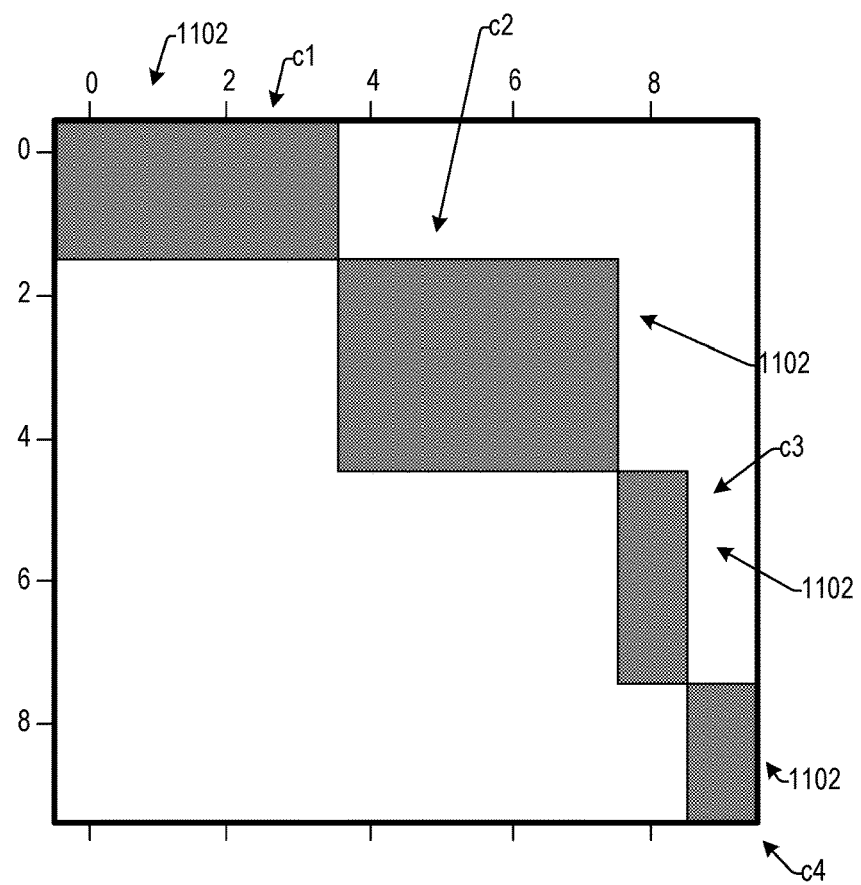
FIG. 11 illustrates an example heat map of the incidence matrix of FIG. 10 after bi-clustering according to some implementations.

After applying a bi-clustering algorithm, such as spectral clustering, the rows and columns of the original incidence matrix may be rearranged and so that the transitions are clustered into a plurality of clusters. FIG. 10 discussed below illustrates the example incidence matrix with four clusters. The four clusters are labeled as c1, c2, c3, and c4 and these four clusters may be used as the new features. If an admission has gone through a transition (e.g., D:5→P:1), the corresponding cluster c1 may have a value of 1 for this admission while the remaining clusters c2, c3, and c4 may have a value of 0. As discussed below, FIG. 11 illustrates an example heat map corresponding the incidence matrix following bi-clustering of the data, and may be presented in a user interface on the display 118 to enable visualization of the bi-clustered features. In addition, as discussed below, FIG. 12 illustrates an example data structure of admission with features generated by bi-clustering that may be generated by the care path pattern recognition module 174.

Figure 13:
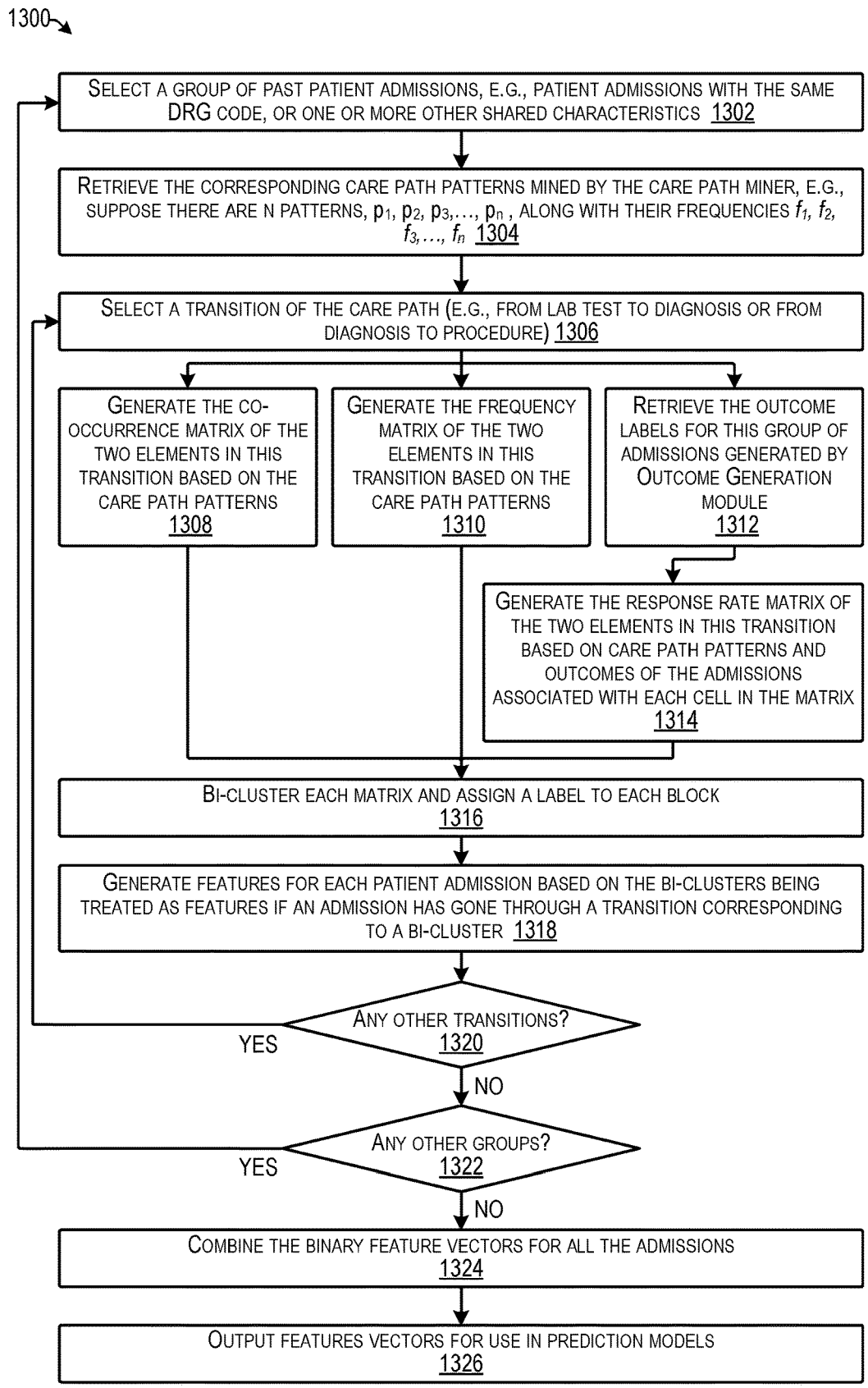
FIG. 13 is a flow diagram illustrating an example process for bi-clustering according to some implementations.

Furthermore, the example above describes clustering the transitions based on the incidence matrix (i.e., option (a) discussed above). However, the care path pattern recognition module 174 may also cluster the transitions based on a transition frequency matrix (i.e., option (b) discussed above) and a transition response rate matrix (i.e., option (c) discussed above) to provide additional features for use in the machine learning models 132. As discussed below, FIG. 13 illustrates an example process for generating the features by bi-clustering care paths according to some implementations. The generated features may be subsequently used for the analytics application(s) 126 and/or 128, as discussed additionally below.

The care path patient profile model builder 176 may be executed to generate a profile for each frequent care path of past patients. For example, when a patient is newly admitted, if the hospital can make certain critical predictions, such as the care path that the patient may be most likely to experience and the length of stay, the prediction may help the healthcare professional to determine the next intervention step, and may also help streamline the hospital operations, such as by being used by the hospital to manage the hospital resources such as beds, staff, medical equipment, medical supplies, and so forth.

The care path patient profile model builder 176 may be executed to configure the service computing device 102 to build and store a profile for each frequent care path experienced by patients in the past. The care path patient profile may include a set of patient characteristics determined to be significant, as well as the interactions among these patient characteristics that are unique or otherwise distinct for each care path pattern. The patient characteristics may include patient demographic information, genetic information, health history, clinical history prior to the admission, and the like. These characteristics may be a common pattern extracted from the received data using supervised machine learning models 132, rather than mere ad-hoc choices. For example, when a patient is newly admitted, the same set of features for this new patient is extracted and compared with the care path patient profile model for each care path pattern so that the hospital can predict more accurately the possible care path for the new patient. With the profiles stored in the system, implementations herein are able to overcome the challenge of not being able to access an admission, discharge, transfer (ADT) system in real time and can still accurately predict the length of stay, patient care requirements, and the like.

In some example herein, building a care path patient profile model may be performed by training a machine learning classifier or other suitable machine learning model 130. For example, the care path patient profile model builder 176 may build a respective classifier as a care path patient profile model for each frequent care path (e.g., the care paths already classified as being frequent care paths by the care path miner 168 above. The care paths mined by the care path miner 168, as well as the features generated by the feature generator 172 in the data mining program 122 may be used as the input to the care path patient profile model builder 176.

As one example, the care path patient profile model builder 176 may select a care path pattern p and may retrieve the admissions that have gone through this care path pattern. For example, suppose that there are n(p) such admissions. The care path patient profile model builder 176 retrieves the features for these n(p) admissions such as from the data structure discussed with respect to FIG. 5 below, as a first feature matrix, such as $$X_{n(p) \times q}^+ = [x_1^+, x_2^+, \ldots, x_q^+].$$

The care path patient profile model builder 176 may randomly select another n(p) admissions that have not gone through this pattern, i.e., are associated with patterns other than the selected pattern. These randomly selected admissions represent negative examples while the admissions with pattern p represent positive examples. The care path patient profile model builder 176 may retrieve the features for these negative examples as a second feature matrix, such as:

$$X_{n(p) \times q}^- = [x_1^-, x_2^-, \ldots, x_q^-]$$

The care path patient profile model builder 176 may stack the features for both positive examples and negative examples as a single feature matrix, such as:

$$X_{2n(p) \times q} = \begin{bmatrix} x_1^+, x_2^+, \ldots, x_q^+ \\ x_1^-, x_2^-, \ldots, x_q^- \end{bmatrix}$$

The care path patient profile model builder 176 may create a label vector of length 2n(p) with the first n(p) elements each denoted as "1" and the last n(p) elements each denoted as "0". The care path patient profile model builder 176 may further denote the label vector as Y=[1, 1, . . . , 1, 0, 0, . . . , 0]$^T$.

The care path patient profile model builder 176 may train a binary classifier on the combined feature matrix $X_{2n(p) \times q}$ and the label vector Y, and may store the machine learning classifier model with the best classification performance as the care path patient profile model for the selected pattern. In the examples herein, the trained classifier model may essentially be a function of a set of characteristics from the patients. In practical implementation, there may be a prediction method employed using the trained model that can be used to predict new data. The care path patient profile model builder 176 may repeat the process for each frequent pattern identified by the care path miner discussed above.

Figure 14:
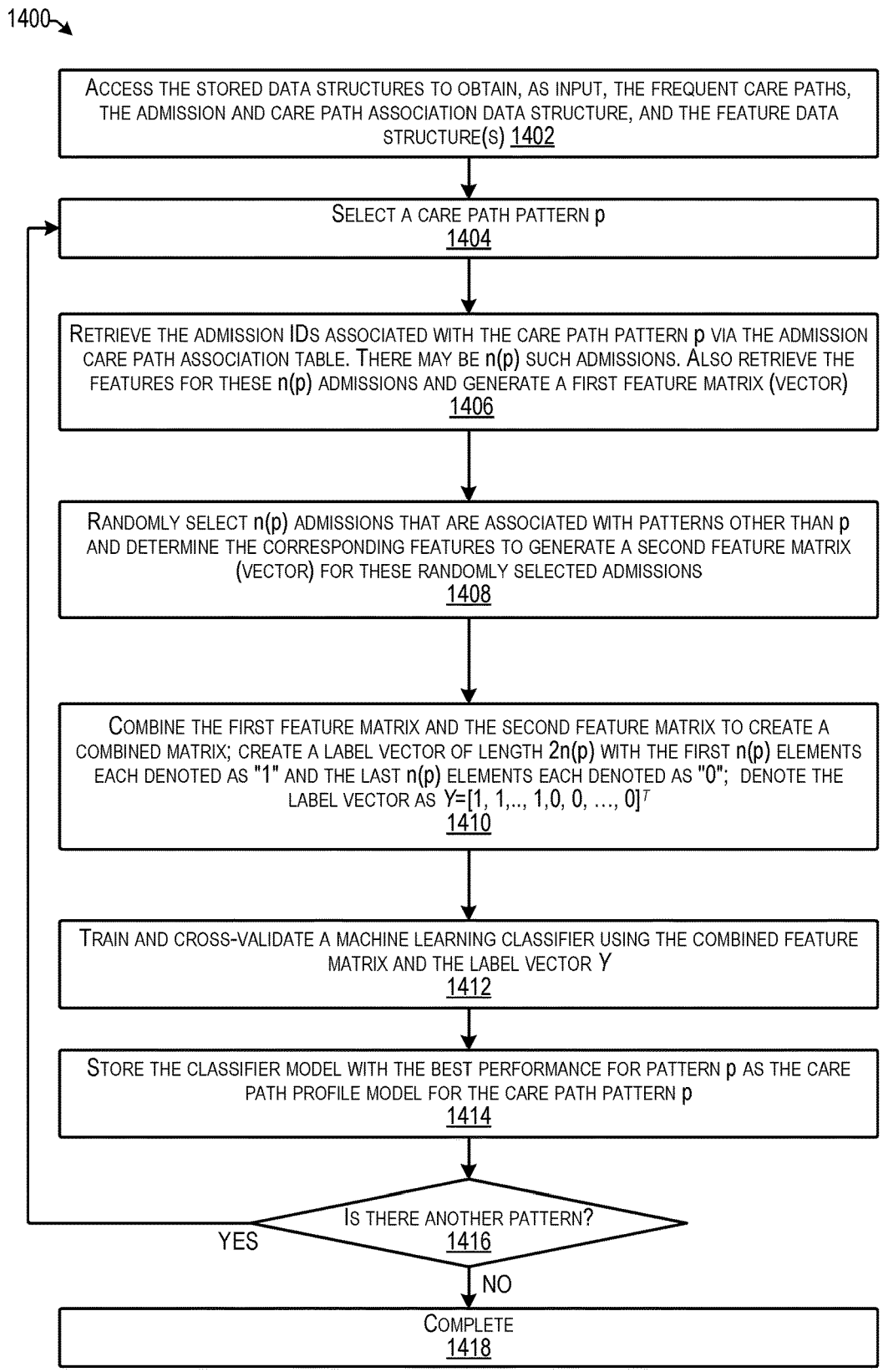
FIG. 14 is a flow diagram illustrating an example process for generating care path patient profile models according to some implementations.

The machine learning models 132 used as the care path patient profile models may be any of many commonly used classification models, such as logistic regression models, random forest models, support vector machine (SVM) models, gradient boosting machine models, or the like. As discussed additionally below, FIG. 14 illustrates an example process for generating a care path patient profile model according to some implementations.

The comparative effectiveness analytics module 178 may be executed to provide insights on the associated probabilities of outcomes or the like, such as probability of re-admission, probability of hospital-acquired infection, probability of mortality, etc., as well as to discover and reduce any inappropriate variations that are not supported on a quality or outcome basis. The comparative effectiveness analytics module 178 may be executed to perform comparative effectiveness analytics by initially selecting a group of patients. For example, the group of patients may have the same DRG code, or may have other specified characteristics in common. The comparative effectiveness analytics module 178 may retrieve the mined care paths associated with this group of patients, such as by accessing the data structure discussed with respect to FIG. 2.

The comparative effectiveness analytics module 178 may further specify a set of risk and cost measures such as re-admission, mortality, length of stay, cost, etc., for determining predicted probabilities therefor, and may calculate the distribution for each specified measure for admissions associated with each care path pattern. In addition, the comparative effectiveness analytics module 178 may calculate summary statistics for each measure distribution. For example, the summary statistics may include a mean, a standard deviation, a median, or other statistical value of interest.

Figure 15:
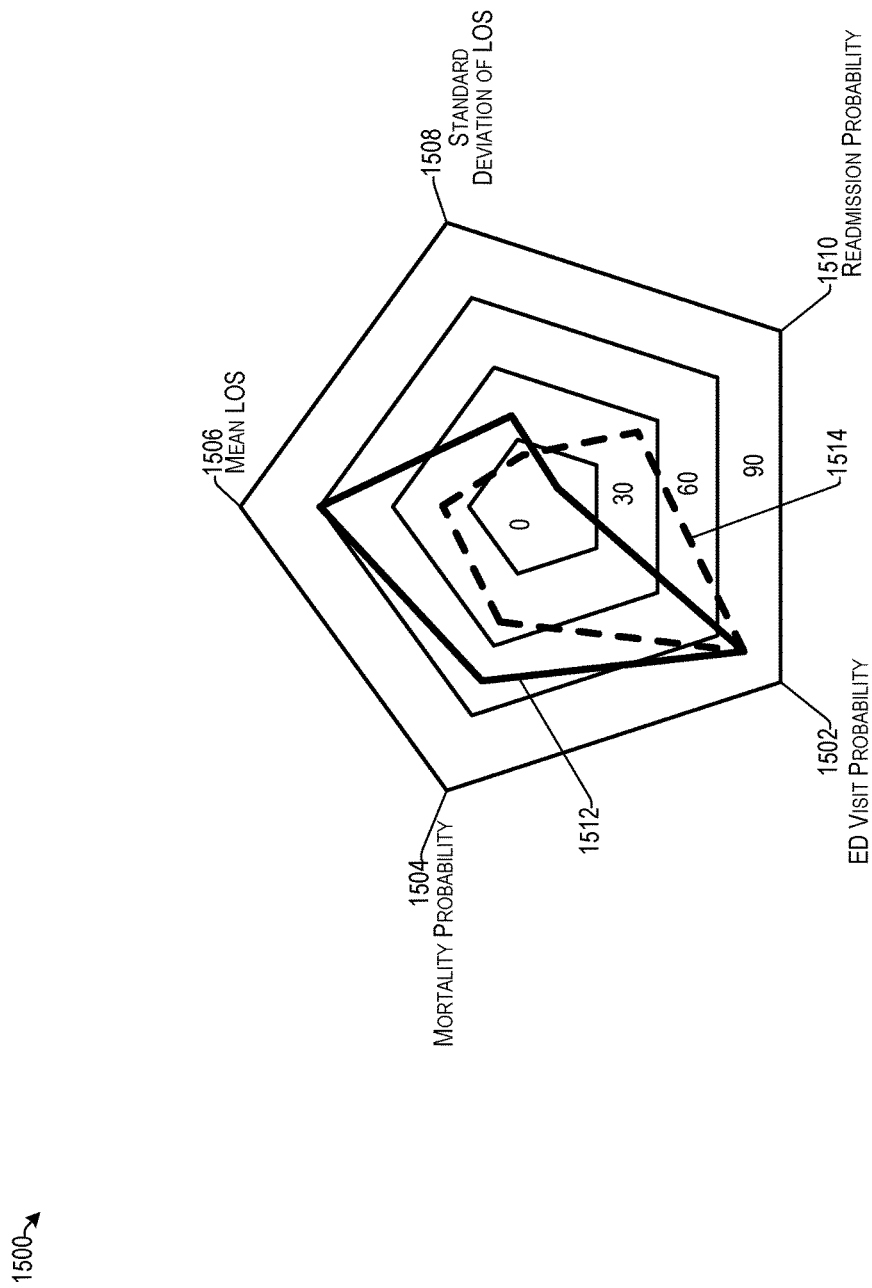
FIG. 15 illustrates an example visualization of comparative effectiveness analysis according to some implementations.

Furthermore, the comparative effectiveness analytics module 178 may generate a visualization of the determined statistics for the specified measure(s) for different care paths, and may present the visualization in a graphic user interface (GUI). As one example, a spider chart may be used to visualize and compare different probabilities for different care path patterns. As discussed additionally below, FIG. 15 illustrates an example visualization that may be used for comparing the various care paths to determine whether one care path may provide a better overall outcome than the other.

As illustrated in FIG. 1, the system 100 provides a care path analytics platform that supports at least two categories of applications: predictive analytics application(s) 126 and prescriptive analytics application(s) 128. The example applications illustrated in this example include the hospital-acquired infection risk prediction application 180, the hospital readmission risk prediction application 182, the emergency department visit prediction application 184, the length of stay (LOS) prediction application 186, the next medical intervention recommendation application 192, the hospital bed management application 188, and the staff planning application 190.

As one example, for the hospital-acquired infection risk prediction application 180, the hospital readmission risk prediction application 182, and the emergency department visit prediction application 184, a binary classification model may be trained first and then the trained model may be used for predicting the target of interest for new patients. Additionally, for the LOS prediction application 186, the processing may be treated as a continuous variable prediction problem.

As one example, let y denote the predictive target of interest. For the hospital-acquired infection risk prediction application 180, the hospital readmission risk prediction application 182, and the emergency department visit prediction application 184, y may be a binary. On the other hand, for the LOS prediction application 186, y may be a positive continuous variable. Because of the similarity among the hospital-acquired infection risk prediction application 180, the hospital readmission risk prediction application 182, and the emergency department visit prediction application 184, the processes for supporting and enhancing this group of applications may be treated as generally the same binary prediction problem based on the results of the care path pattern recognition module 174. On the other hand, as discussed below, the application the LOS prediction application may use the care path patient profile models determined by the care path patient profile model builder.

In addition, the next medical intervention recommendation application 192 may be executed using a direct application of the outputs of the care path patient profile model builder 176 and the comparative effectiveness analytics module 178. Furthermore, the other prescriptive analytics applications, the hospital bed management application 188 and the staff planning application 190, are about hospital resource management. One of the factors for successful resource management is to the ability to accurately predict the demand. Accordingly, the output of the LOS prediction application 186 may be used as an input for these applications.

The binary predictive applications (i.e., the hospital-acquired infection risk prediction application 180, the hospital readmission risk prediction application 182, and the emergency department visit prediction application 184) involve two stages, namely, a training stage and a prediction stage.

In the training stage, a prediction target may be specified. For example, the prediction target may be one or more of a probability of a hospital-acquired infection, a probability of hospital readmission, or a probability of an emergency department visit. Further, the application may select a group of patients and may access the data structures to obtain corresponding data provided by the data management program 120 and the data mining program 122. In addition, the outcome generator 170 may be executed as described with respect to, e.g., FIGS. 1 and 4 for generating an outcome label vector. Further, the care path miner 168 may be executed as described with respect to FIGS. 1 and 2 to identify care path patterns associated with the patients in the selected group of patients.

Furthermore, the feature generator 172 may be executed as described with respect to FIGS. 1, 6 and 7 to generate basic features for the patients in the selected group of patients. Additionally, advanced cross-source features based on the care path patterns are generated by executing the care path pattern recognition module 174. As one example, a technique for generating the advanced cross sourced features may include extracting the care path for a patient admission in the group of patients, retrieving a binary feature for this care path from the care path patterns determined by the care path pattern recognition module 174, retrieving the multi-class categorical feature for this care path, and outputting both types of features for this group of patients. Further, the application may merge the basic features and the advanced features to form a feature matrix.

The application may train and cross validate a binary machine learning classifier using the feature matrix and the outcome label vector. The application may store the classifier model with the best performance for use in the prediction stage by the respective application. As mentioned above, the application may be one of the hospital-acquired infection risk prediction application 180, the hospital readmission risk prediction application 182, or the emergency department visit prediction application 184. An example flow of the process for training is illustrated with respect to FIG. 16 discussed below.

Furthermore, during the prediction stage of a binary predictive application (i.e., one of the hospital-acquired infection risk prediction application 180, the hospital readmission risk prediction application 182, or the emergency department visit prediction application 184), the application may receive, as input, a new patient admission, discharge or the like, for prediction. In response, the feature generator 172 may be executed as described above with respect to FIGS. 1, 6, and 7 to generate basic features for the particular patient. Additionally, the care path pattern recognition module 174 may be executed for generating the advanced features. As one example, the care path pattern recognition module may extract the care path for this new patient admission, retrieve the binary features for this care path from the patterns extracted by the care path pattern recognition module, retrieve the multi-class categorical features for this care path from the patterns mined by the care path pattern recognition module, and output both types of features for this admission or discharge.

The binary application may merge the basic features and the advanced features to generate a full set of features for this admission or discharge. The application may input the generated full set of features into the trained machine learning prediction model for the respective application to determine a probability of the outcome for the selected admission or discharge, and may output the predicted probability determined using the trained machine learning prediction model. An example flow of the process for prediction is illustrated with respect to FIG. 17, as discussed below. As mentioned, the process may be executed using any of the hospital-acquired infection risk prediction application 180, the hospital readmission risk prediction application 182, or the emergency department visit prediction application 184.

In some examples, the length of stay (LOS) prediction application 186 may be configured to perform at least one of two non-parametric estimation methods. For instance, the estimation methods herein do not rely on any assumption on the distribution of the LOS. The set of care path patient profile models built by the care path patient profile builder 176 may be used for predicting LOS. These two methods are similar except that the second method has additional steps and is more computationally expensive in order to achieve better performance.

For instance, the first method may use an empirical distribution of the most likely care path to predict the length of stay for a new patient admission. The second method uses a weighted mixture of the distributions of all possible care paths. The output of the LOS prediction application 186 may be a distribution of the predicted LOS for a particular patient, rather than a single statistic, such as the mean or the median, to offer the flexibility for further estimation used in other applications, such as the hospital bed management application 188 and the staff planning application 190.

When executing the LOS prediction application 186, the LOS prediction application 186 may receive, as input, a new patient admission, and may generate features for this admission, such as by executing the feature generator 172 as described above with respect to FIGS. 1, 6, and 7 to generate basic features for the particular admission. The LOS prediction application 186 may use the saved care path patient profile models one by one to generate predictions based on the features for this admission. Accordingly, for each model, a probability may be generated. For instance, suppose there are altogether n care path patient profile models and the predicted probabilities are $p_1, p_2, \ldots, p_n$. At this point, the LOS prediction application 186 may execute either the first method described above, or the second method.

When executing the first method, the LOS prediction application 186 may calculate the empirical distribution of the LOS of historical admissions associated with care path k, where $p_k=\max(p_1, p_2, \ldots, p_n)$, and may output the distribution of LOS for care path k as the prediction of the LOS for this admission. On the other hand, when executing the second method, the LOS prediction application 186 may calculate a weight for each care path. For example, the weight for each care path may be calculated based on $$w_i = \frac{p_i}{\sum_{j=1}^{n} p_j},$$

i=1, ..., n in which $w_i$ is the weight of care path i. The LOS prediction application 186 may also calculate the empirical distribution of the LOS of historical admissions associated with each care path. For the empirical distribution of LOS of historical admissions, the LOS prediction application 186 may be configured to apply kernel density estimation or other suitable estimation techniques. For example, suppose the distribution of LOS for care path i is $f_i(x)$. The LOS prediction application 186 may calculate the weighted mixture distribution based on the calculated weights and the empirical distribution. As an example, $F(x)=\Sigma_{i=1}^{n} w_i f_i(x)$ where F(x) is the weighted mixture distribution. Finally, the LOS prediction application 186 may output the weighted mixture distribution F(x) as the prediction of the LOS for this admission. A flow diagram of the process including the two methods is discussed below with respect to FIG. 18.

The next medical intervention recommendation application 192 may determine a next recommended medical intervention based on a direct application of the care path patient profile models and the care path comparative effectiveness analytics. The procedure of predicting the most likely care path for a newly admitted patient using the care path patient profiles may include running the feature generator 172 of the data mining program 122 to generate features for a selected patient admission. The next medical intervention recommendation application 192 may input the generated features as input to the saved care path patient profile models one by one to generate predictions based on the features generated for this admission. For each care path patient profile model, a probability may be generated. This probability may indicate how likely this admission will follow a particular care path. The next medical intervention recommendation application 192 may rank all the probabilities generated and output the top k models with the highest probabilities.

The value of k may be configurable by the user. Accordingly, k may be 1 or some integer greater than 1. By outputting more than one most likely care path, the next medical intervention recommendation application 192 gives a medical professional flexibility in selecting a care path that may include, in the medical professional's opinion, the most appropriate tradeoff among different risks based on the insights provided by the care path comparative effectiveness analytics module 178.

In addition to the top k most likely care paths for this new admission, the associated risk and cost metrics for these top k care paths may also be determined, which might also assist the medical professional in making an informed decision on the next intervention. A flow diagram of the process is discussed below with respect to FIG. 19. In addition, a graphic user interface (GUI) for enabling visualization of the predictions and selecting an optimal care path is discussed below with respect to FIG. 20.

The hospital bed management application 188 and the staff planning application 190 may receive as input the output of the LOS prediction application 186. In some examples herein, the demand prediction for certain resources (e.g., hospital beds, hospital staff, hospital equipment, etc.) may be determined based on an aggregation of individual patient LOS predictions. As mentioned above, the LOS prediction application 186 may be configured to output a distribution of predicted LOS for each admission. To perform aggregation of these multiple distributions, the hospital bed management application 188 and/or the staff planning application 190 may first determine an estimated probability that the LOS is at least i days, for each new patient. As one example, a configurable percentile for the demand for the specified resource on day i from these patients, such as the 50th, 75th, or 90th percentile may be employed. For example, if a conservative approach to resource management is desired, then a higher percentile, e.g., the 90th percentile may be employed. On the other hand, if a more optimistic approach to resource management is desired, then a lower percentile, for example, the 50th percentile (i.e., the median) may be employed.

As an example, a user may execute one of the hospital bed management application 188 or the staff planning application 190, and may receive, as input, a group of new patient admissions for a day (day 0) that share a resource. In addition, the LOS prediction application 186 discussed above with respect to FIG. 1 may be executed for each admission to determine the LOS distribution for each admission in the group. Further, the application may estimate the probability that each individual LOS is at least i. As one example, suppose there are a total of M new patients, and for each individual patient admission m, the estimated probability that the LOS is at least i is $x_m(i)$. In addition, the application may calculate the specified percentile $D_i$ of the aggregate demand from the new patient admissions on a selected day i, with the $m^{th}$ admission contributing to this aggregate if its LOS is at least i. As one example, $D_i$ may be calculated as the specified percentile of the sum of M independent binary (0/1) random variables with expected values $x_m(i)$, m=1, 2, . . . , M.

The application may output the predicted demand $D_i$ for resources for one or more selected days i based on the received new patient admissions. Furthermore, the application may perform at least one action based on the predicted demand. For example, if the hospital bed management application 188 is being executed, the hospital bed management application 188 may reserve a required number of beds based on the predicted demand for the beds. Similarly, if the staff planning application 190 is being executed, the staff planning application 190 may schedule a required number of staff employees to work at specified times based on the predicted demand for staffing at those times. An example flow diagram illustrating the process for resource management is discussed below with respect to FIG. 21.

FIG. 2 illustrates an example data structure 200 of mined care path patterns for a group of patients according to some implementations. As mentioned above, the data structure 200 may be generated by the care path miner 168 of the data mining program 122 discussed above with respect to FIG. 1. The care path miner 168 may model the care path as a sequence of lab→diagnosis→procedure, which covers the major interventions that patients experience during their stay with a hospital. In the example of FIG. 2, the data structure 200 includes a detected pattern 202, the lab test(s) 204 corresponding to the respective pattern, the diagnosis code 206 corresponding to the respective pattern, the procedure code 208 corresponding to the respective pattern, and the frequency 210 of each respective pattern.

FIG. 3 illustrates an example data structure 300 of admission and care path associations according to some implementations. The data structure 300 may be generated by the data miner 168 of the data mining program 122 to be used by the core analytics program, as discussed above. For example, the care path miner 168 may be configured to determine the association between admissions to the hospital and the care path patterns determined in the data structure 200 discussed above with respect to FIG. 2, and may store these associations in the data structure 300 of FIG. 3. Thus, the data structure 300 includes an admission identifier 302 that represents the admission of a particular patient to the hospital, and a care path pattern 304 that indicates the care path provided to the patient to which the particular admission corresponds.

FIG. 4 illustrates an example data structure 400 of outcomes that result in readmission according to some implementations. The data structure 400 may be generated by the outcome generator 170 of the data mining program 122, as discussed above with respect to FIG. 1. Some examples herein may use a binary variable to represent hospital-acquired infection and readmission. That is, for each admission, if a patient was readmitted to the hospital within a pre-defined period after the discharge, the corresponding outcome variable for this admission is 1, otherwise, 0.

In the illustrated example, the admission identifier (ID) is indicated at 402, and a corresponding outcome is indicated at 404. In this example, the outcome is re-admission. Further, as discussed above, other types of outcomes may be included in the data structure 400. For example, if a patient acquired a type of infection of interest during the stay (not shown in FIG. 4), the corresponding outcome variable for this admission is 1, otherwise, 0.

FIG. 5 illustrates an example data structure 500 of example features according to some implementations. The data structure 500 may be generated by the feature generator 172 of the data mining program 122 discussed above with respect to FIG. 1. As discussed above, to facilitate building a care path patient profile model by the core analytics program 124, the feature generator 172 may generate the potential patient features at each admission level. The feature generator 172 may generate the features mainly from each individual data source, e.g., the EHR system, the ADT system, clinical information systems, etc. These may be referred to as basic features. In the illustrated example, the data structure 500 includes a category of features, as indicated at 502, and a list of features corresponding to each category, as indicated at 504. Examples of categories 502 may include sociodemographic features, utilization features, and overall health and clinical history features.

FIG. 6 illustrates an example data structure 600 of example admissions with generated features according to some implementations. The data structure 600 may be generated for a group of index admissions as discussed above with respect to FIG. 1. In this example, the data structure 600 includes a respective admission number 602; a respective DRG code 604 for the admission number; a respective care path pattern 606 for the respective admission number; a value t* as indicated at 608 indicating the threshold number of patterns for being classified as a frequent pattern, and flow feature 610, which may be 1 when the pattern is frequent and 0 when the pattern is not frequent.

FIGS. 7, 13, 14, and 16-20 are flow diagrams illustrating example processes according to some implementations. The processes are illustrated as collections of blocks in logical flow diagrams, which represent a sequence of operations, some or all of which can be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, systems and devices described in the examples herein, although the processes may be implemented in a wide variety of other environments, systems and devices.

FIG. 7 is a flow diagram illustrating an example process 700 for clustering care paths based on frequency according to some implementations. In some examples, the process 700 may be executed by the service computing device(s) 102 or other suitable computing device(s), such as by execution of the care path pattern recognition module 174 and other modules discussed above.

At 702, the computing device may select a group of past patient admissions with at least one shared characteristic (e.g., past patient admissions with the same DRG code). For example, there may be K such patient admissions.

At 704, for these K patient admissions, the computing device may retrieve the corresponding care path patterns $p_1, p_2, p_3, \ldots, p_n$ and the associated frequencies $f_1, f_2, f_3, \ldots, f_n$. For example, the care path miner may have previously determined n care path patterns with the associated frequency $f_1, f_2, f_3, \ldots, f_n$, and may have generated the data structure 200 discussed above with respect to FIG. 2.

At 706, the computing device may, for a threshold t, if $f_i \geq t$, assign a value 1 to all patients admitted that went through pattern $p_i$; otherwise assign a value of 0.

At 708, the computing device may generate the binary feature vector based on the assigned values. For example, the computing device may denote $X(t)=\{x_1, x_2, \ldots, x_K\}$ as the binary feature vector generated when the threshold is set at t.

At 710, the computing device may retrieve the outcome labels for this group of patients. For example, the outcome generator of the data mining program may have previously determined the outcome labels for a corresponding prediction target, e.g., as discussed above with respect to FIGS. 1 and 4. Suppose in this example that the outcome label is $Y=\{y_1, y_2, \ldots, y_K\}$.

At 712, the computing device may find an optimized threshold t* on the pattern frequency. To maximize the mutual information between the feature vector and Y, the formula t*=argmax (mutual information (Y, X(t))) may be applied. The computing device may keep the corresponding feature vector for these K patients: $X(t^*)=\{x_1, x_2, \ldots, x_K\}$.

At 714, the computing device may determine whether there are any other groups of patients to process. If so, the process returns to 702; if not, the process goes to 716.

At 716, the computing device may combine the binary feature vectors for all the patient admissions for all the groups. The features generated for all the groups of patient admissions may be added to a data structure, such as is described with respect to FIG. 6.

At 718, the computing device may output the feature vectors for use in prediction models.

FIG. 8 illustrates an example data structure of an incidence matrix 800 including transitions from diagnosis to procedures according to some implementations. In this example incidence matrix, the rows 802 represent diagnosis codes, such as codes D:1 to D:10, and the columns 804 represent procedure codes, such as codes P:1 to P:10, for a group of patient admissions. The incidence matrix 800 represents the respective transitions before bi-clustering is applied.

Figure 9:
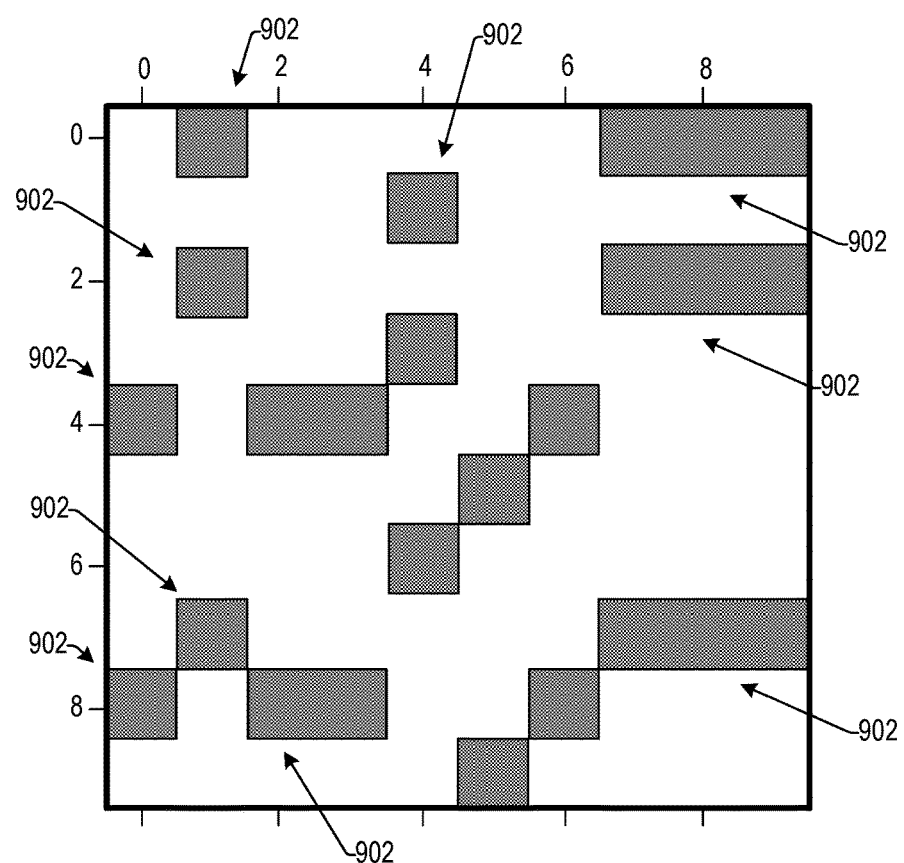
FIG. 9 illustrates an example heat map of the incidence matrix of FIG. 8 according to some implementations.

FIG. 9 illustrates an example heat map 900 of the incidence matrix 800 of FIG. 8 according to some implementations. In this example, a block 902 is placed at each location of a "1" in the incidence matrix 800 and a block is not placed at the location of a "0" in the incidence matrix 800. The heat map represents the respective transitions before bi-clustering is applied.

FIG. 10 illustrates an example data structure of the incidence matrix 800 of FIG. 8 after bi-clustering according to some implementations. In this example of the incidence matrix 800, the rows 802 continue to represent the diagnosis codes, such as codes D:1 to D:10, and the columns 804 continue to represent the procedure codes, such as codes P:1 to P:10, for a group of patients. After applying a bi-clustering algorithm, such as spectral clustering, the rows 802 and columns 804 of the incidence matrix 800 are rearranged so that the transitions in the incidence matrix 800 are now clustered into four clusters 1002, 1004, 1006 and 1008. These four clusters are labeled as c1, c2, c3 and c4, respectively, and these four clusters can be used as the new features. For example, if an admission has gone through a transition (e.g., D:5→P:1), the corresponding cluster c1 will have a value of 1 for this admission while the rest of the clusters c2, c3, and c4 will have a value of 0.

FIG. 11 illustrates an example heat map 1100 of the incidence matrix 800 of FIG. 10 after bi-clustering according to some implementations. In this example, a block 1102 is placed at each location of a "1" in the incidence matrix 800 of FIG. 10, and a block is not placed at the location of a "0" in the incidence matrix 800 of FIG. 10.

FIG. 12 illustrates an example data structure 1200 of admissions with features generated using bi-clustering according to some implementations. In this example, the care path pattern recognition module 174 may cluster the transitions based on an incidence matrix, such as the incidence matrix 800 discussed above with respect to FIGS. 8 and 10. In other examples, the care path pattern recognition module may cluster the transitions based on a transition frequency matrix or a transition response rate matrix, as discussed above with respect to FIG. 1. In the illustrated example, the data structure 1200 includes an admission number 1202, a corresponding feature 1204 of diagnosis→procedure corresponding to cluster c1; a corresponding feature 1206 of diagnosis→procedure corresponding to cluster c2; a corresponding feature 1208 of diagnosis→procedure corresponding to cluster c3; and a corresponding feature 1210 of diagnosis→procedure corresponding to cluster c4.

FIG. 13 is a flow diagram illustrating an example process 1300 for bi-clustering according to some implementations. In some examples, the process 1300 may be executed by the service computing device(s) 102 or other suitable computing device(s) such as by executing the care path pattern recognition module 174 discussed above with respect to FIG. 1.

At 1302, the computing device may select a group of past patient admissions, e.g., past patient admissions with the same DRG code, or one or more other shared characteristics.

At 1304, the computing device may retrieve the corresponding care path patterns mined by the care path miner, e.g., suppose there are n care path patterns, $p_1, p_2, p_3, \ldots, p_n$, along with their frequencies $f_1, f_2, f_3, \ldots, f_n$.

At 1306, the computing device may select a transition of the care path (e.g., from lab test to diagnosis or from diagnosis to procedure).

At 1308, the computing device may generate the co-occurrence matrix of the two elements in this transition based on the care path patterns.

At 1310, the computing device may generate the frequency matrix of the two elements in this transition based on the care path patterns.

At 1312, the computing device may retrieve the outcome labels for this group of patients, e.g., as previously generated by outcome generator 170, as discussed above with respect to FIGS. 1 and 4.

At 1314, the computing device may generate the response rate matrix of the two elements in this transition based on the care path patterns and the outcomes of the patient admissions associated with each cell in the matrix.

At 1316, the computing device may bi-cluster each matrix and assign a label to each block, e.g., 1 or 0.

At 1318, the computing device may generate features for each patient in the group as in the data structure illustrated in FIG. 12, i.e., based on the bi-clusters being treated as features if an admission has gone through a transition corresponding to a bi-cluster.

At 1320, the computing device may determine whether there are any other transitions to process. If so, the process returns to 1306; if not, the process goes to 1322.

At 1322, the computing device may determine whether there are any more groups of patients to process. If so, the process returns to 1302; if not, the process goes to 1324.

At 1324, the computing device may combine the binary feature vectors for all the admissions. The features generated for a group of index admissions may be added to a data structure, such as is described with respect to FIG. 12.

At 1318, the computing device may output the feature vectors for use in prediction models.

FIG. 14 is a flow diagram illustrating an example process 1400 for generating care path patient profile models according to some implementations. In some examples, the process 1400 may be executed by the service computing device(s) 102 or other suitable computing device(s) by executing the care path patient profile model builder 176 discussed above with respect to FIG. 1.

At 1402, the computing device may access the stored data structures to obtain, as input, the frequent care paths mined by the care path miner, the admission and care path association data structure, and the feature data structure(s) generated by the feature generation module and/or the care path pattern recognition module.

At 1404, the computing device may select a care path pattern p from the frequent care paths.

At 1406, the computing device may retrieve the admission IDs associated with the selected care path p via the admission care path association data structure (e.g., as illustrated in FIG. 3 above). For example, there may be n(p) such admissions. In addition, the computing device may retrieve the features for these n(p) admissions and generate a feature matrix (vector) as discussed above, such as $X_{n(p) \times q}^{+} = [x_1^+, x_2^+, \ldots, x_q^+]$ At 1408, the computing device may randomly select n(p) admissions that are aassociated with patterns other than p and determine the corresponding features. The computing device may generate a second feature matrix (vector) for these randomly selected admissions as discussed above, such as $X_{n(p) \times q}^{-} = [x_1^-, x_2^-, \ldots, x_q^-]$.

At 1410, the computing device may stack the first feature matrix and the second feature matrix to create a combined matrix. For example, the combined matrix may be expressed as:

$$X_{2n(p) \times q} = \begin{bmatrix} x_1^+, x_2^+, \ldots, x_q^+ \\ x_1^-, x_2^-, \ldots, x_q^- \end{bmatrix}$$

The computing device may further create a label vector of length 2n(p) with the first n(p) elements each denoted as "1" and the last n(p) elements each denoted as "0". The care path patient profile model builder 176 may further denote the label vector as $Y=[1, 1, \ldots, 1, 0, 0, \ldots, 0]^T$.

At 1412, the computing device may train and cross-validate a machine learning classifier using the combined feature matrix and the label vector Y.

At 1414, the computing device may store the classifier model with the best performance for the selected care path pattern p as M(p), i.e., the care path patient profile model for the selected pattern.

At 1416, the computing device may determine whether there is another pattern to be processed. If so, the process goes back to 1404; if not, the process goes to 1418.

At 1418, the computing device may complete the process.

FIG. 15 illustrates an example visualization 1500 of comparative effectiveness analysis according to some implementations. In this example, a spider chart is presented as the visualization 1500, although other types of visualizations may be used. The visualization 1500 includes a metric for emergency department (ED) visit probability, as indicated at 1502, a metric for mortality probability, as indicated at 1504, a metric for mean length of stay (LOS), as indicated at 1506, a metric for standard deviation of LOS, as indicated at 1508, and a metric for readmission probability 1510. A first distribution of metrics for a first care path is indicated at 1512, and second distribution of metrics for a second care path is indicated at 1514. Further, while five metrics and two care paths are illustrated in this example, more or fewer of each may be illustrated in other examples, as will be apparent to those of skill in the art having the benefit of the disclosure herein.

Figure 16:
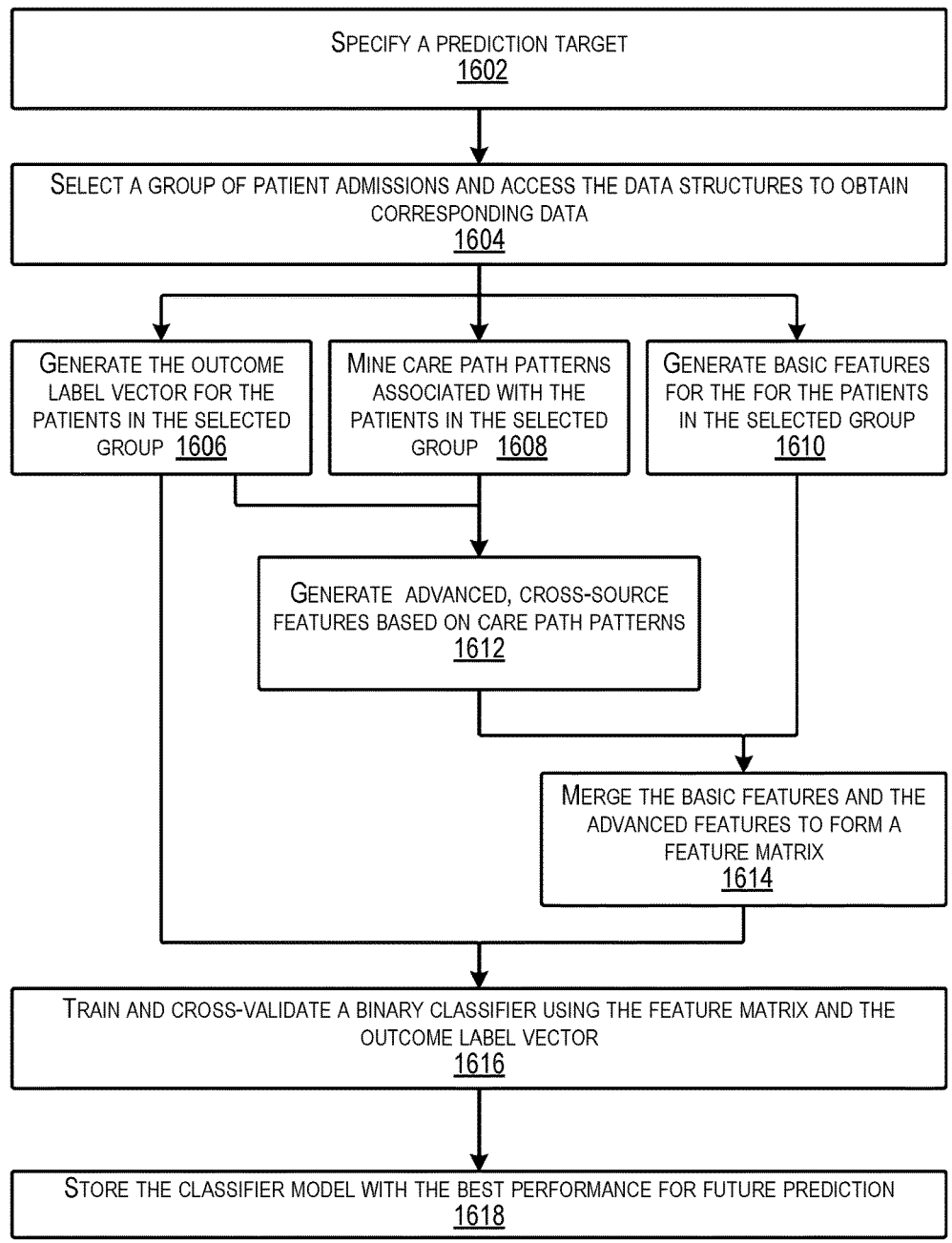
FIG. 16 is a flow diagram illustrating an example process for the training stage for a binary predictive application according to some implementations.

FIG. 16 is a flow diagram illustrating an example process 1600 for the training stage for a binary predictive application according to some implementations. In some examples, the process 1600 may be executed by the service computing device(s) 102 or other suitable computing device(s), such as by executing one of the hospital-acquired infection risk prediction application 180, the hospital readmission risk prediction application 182, or the emergency department visit prediction application 184.

At 1602, the computing device may specify a prediction target. For example, the prediction target may be one or more of a probability of a hospital-acquired infection, a probability of hospital readmission, or a probability of an emergency department visit.

At 1604, the computing device may select a group of patient admissions and may access the data structures to obtain corresponding data provided by the data management program 120 and the data mining program 122.

At 1606, the computing device may generate the outcome label vector for the patients in the selected group of patients. For example, the outcome generator 170 may be executed as described above with respect to, e.g., FIGS. 1 and 4 for generating an outcome label vector.

At 1608, the computing device may mine the care path patterns associated with the patients in the selected group of patients. For example, the care path miner 168 may be executed as described above with respect to FIGS. 1 and 2 to identify care path patterns associated with the patients in the selected group of patients.

At 1610, the computing device may generate basic features for the patients in the selected group of patients. For example, the feature generator 172 may be executed as described above with respect to FIGS. 1, 6 and 7 to generate basic features for the patients in the selected group of patients.

At 1612, the computing device may generate advanced cross-source features based on the care path patterns. As one example, a technique for generating the advanced cross sourced features may include extracting the care path for a respective patient admission, retrieving a binary feature for this care path from the care path patterns determined by the care path pattern recognition module 174, retrieving the multi-class categorical feature for this care path from the care path patterns determined by the care path pattern recognition module 174, and outputting both types of features for this patient admission.

At 1614, the computing device may merge the basic features and the advanced features to form a feature matrix.

At 1616, the computing device may train and cross validate a binary machine learning classifier using the feature matrix and the outcome label vector.

At 1618, the computing device may store the classifier model with the best performance for use in the prediction stage by the respective one of the hospital-acquired infection risk prediction application 180, the hospital readmission risk prediction application 182, or the emergency department visit prediction application 184.

Figure 17:
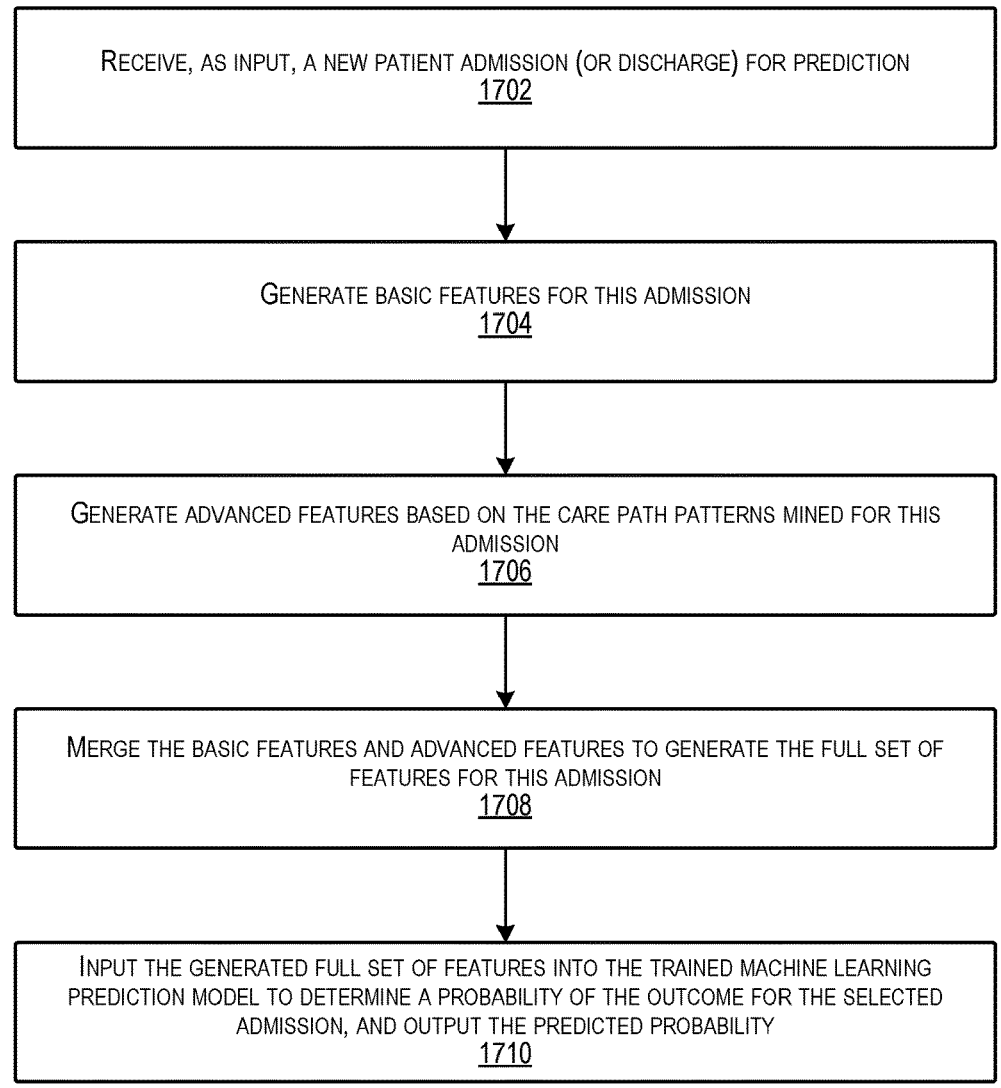
FIG. 17 is a flow diagram illustrating an example process for the prediction stage of a binary predictive application according to some implementations.

FIG. 17 is a flow diagram illustrating an example process 1700 for the prediction stage of a binary predictive application according to some implementations. In some examples, the process 1700 may be executed by the service computing device(s) 102 or other suitable computing device(s), such as by executing one of the hospital-acquired infection risk prediction application 180, the hospital readmission risk prediction application 182, or the emergency department visit prediction application 184.

At 1702, the computing device may receive as input, a new patient admission or discharge for prediction. In the case of a discharge, the corresponding patient admission may be located and used as the input.

At 1704, the computing device may generate basic features for this admission. For example, the feature generator 172 may be executed as described above with respect to FIGS. 1, 6, and 7 to generate basic features for the particular patient.

At 1706, the computing device may generate advanced features for the new patient. For example, the computing device may execute the care path pattern recognition module 174 for generating the advanced features. As one example, the care path pattern recognition module may extract the care path for this new patient admission, retrieve the binary feature for this care path from the patterns extracted by the care path pattern recognition module, retrieve the multi-class categorical feature for this care path from the patterns mined by the care path pattern recognition module, and output both types of features for this admission or discharge.

At 1708, the computing device may merge the basic features and the advanced features to generate a full set of features for this admission or discharge.

At 1710, the computing device may input the generated full set of features into the trained machine learning prediction model for the respective application to determine a probability of the outcome for the selected admission, and may output the predicted probability determined using the trained machine learning prediction model.

Figure 18:
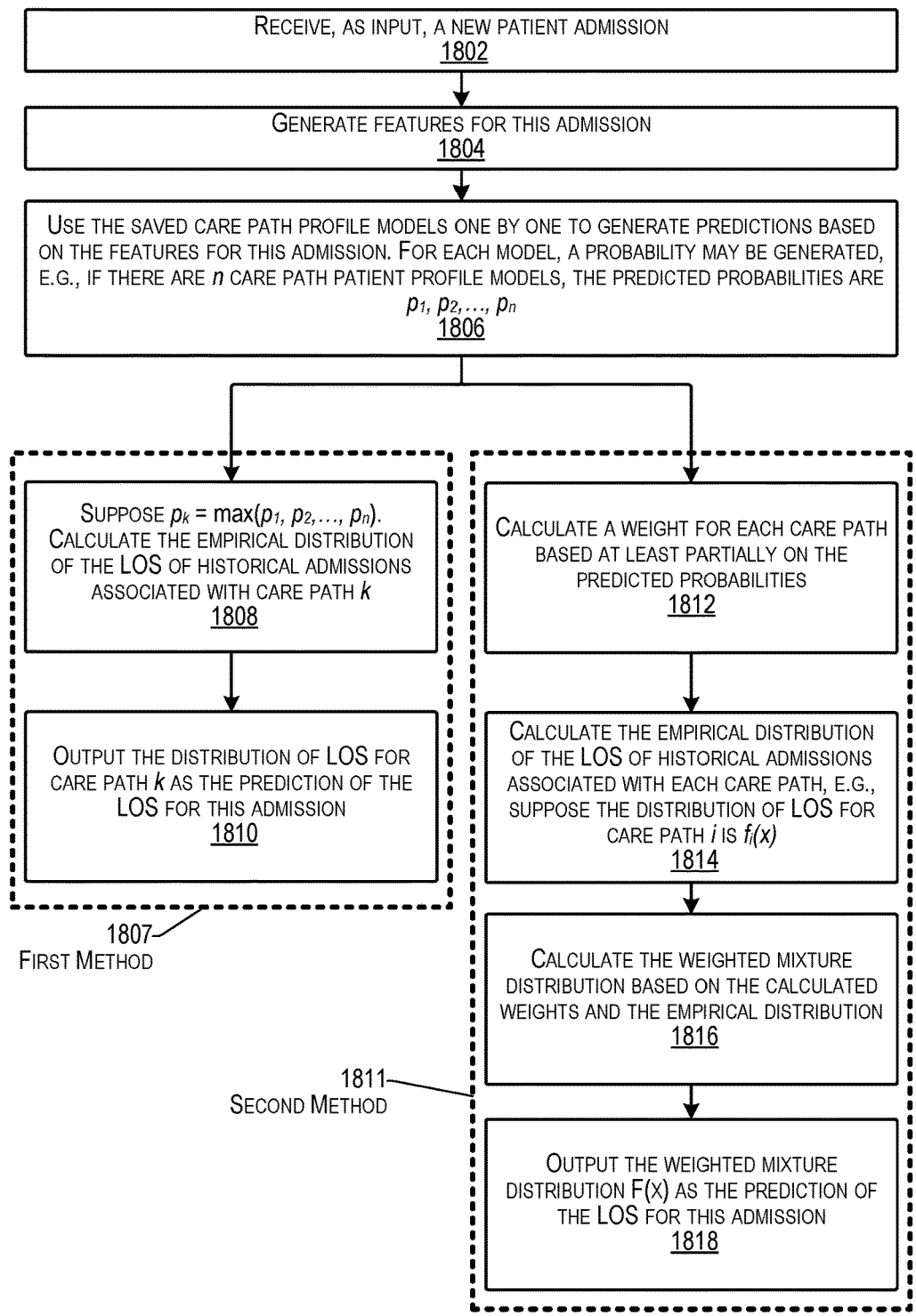
FIG. 18 is a flow diagram illustrating an example process for length of stay (LOS) prediction according to some implementations.

FIG. 18 is a flow diagram illustrating an example process 1800 for length of stay (LOS) prediction according to some implementations. In some examples, the process 1800 may be executed by the service computing device(s) 102 or other suitable computing device(s) by executing the length of stay prediction application 186.

At 1802, the computing device may receive, as input, a new patient admission.

At 1804, the computing device may generate features for this admission. For example, using the techniques discussed above, the feature generator 172 may be executed as described above with respect to FIGS. 1, 6, and 7 to generate basic features for the particular admission. In some examples, advanced features may also be generated as discussed above, e.g., with respect to FIGS. 16 and 17.

At 1806, the computing device may use the saved care path patient profile models one by one to generate predictions based on the features for this admission. For each model, a probability may be generated. Suppose there are altogether n care path patient profile models and the predicted probabilities are $p_1, p_2, \ldots, p_n$. Following 1806, the process may execute a first method 1807 that includes blocks 1808 and 1810, or a second method 1811 that includes blocks 1812, 1814, 1816, and 1818.

At 1808, the computing device may calculate the empirical distribution of the LOS of historical admissions associated with care path k, where $p_k = \max(p_1, p_2, \ldots, p_n)$.

At 1810, the computing device may output the distribution of LOS for care path k as the prediction of the LOS for this admission.

At 1812, the computing device may calculate a weight for each care path based at least partially on the predicted probabilities. For example, the weight for each care path may be calculated based on $$w_i = \frac{p_i}{\sum_{j=1}^{n} p_j},$$

i=1, ..., n in which $w_i$ is the weight of a selected care path.

At 1814, the computing device may calculate the empirical distribution of the LOS of historical admissions associated with each care path. For example, suppose the distribution of LOS for care path i is $f_i(x)$.

At 1816, the computing device may calculate the weighted mixture distribution based on the calculated weights and the empirical distribution. As an example, $F(x)=\sum_{i=1}^{n} w_i f_i(x)$ where $F(x)$ is the weighted mixture distribution.

At 1818, the computing device may output the weighted mixture distribution $F(x)$ as the prediction of the LOS for this admission.

Figure 19:
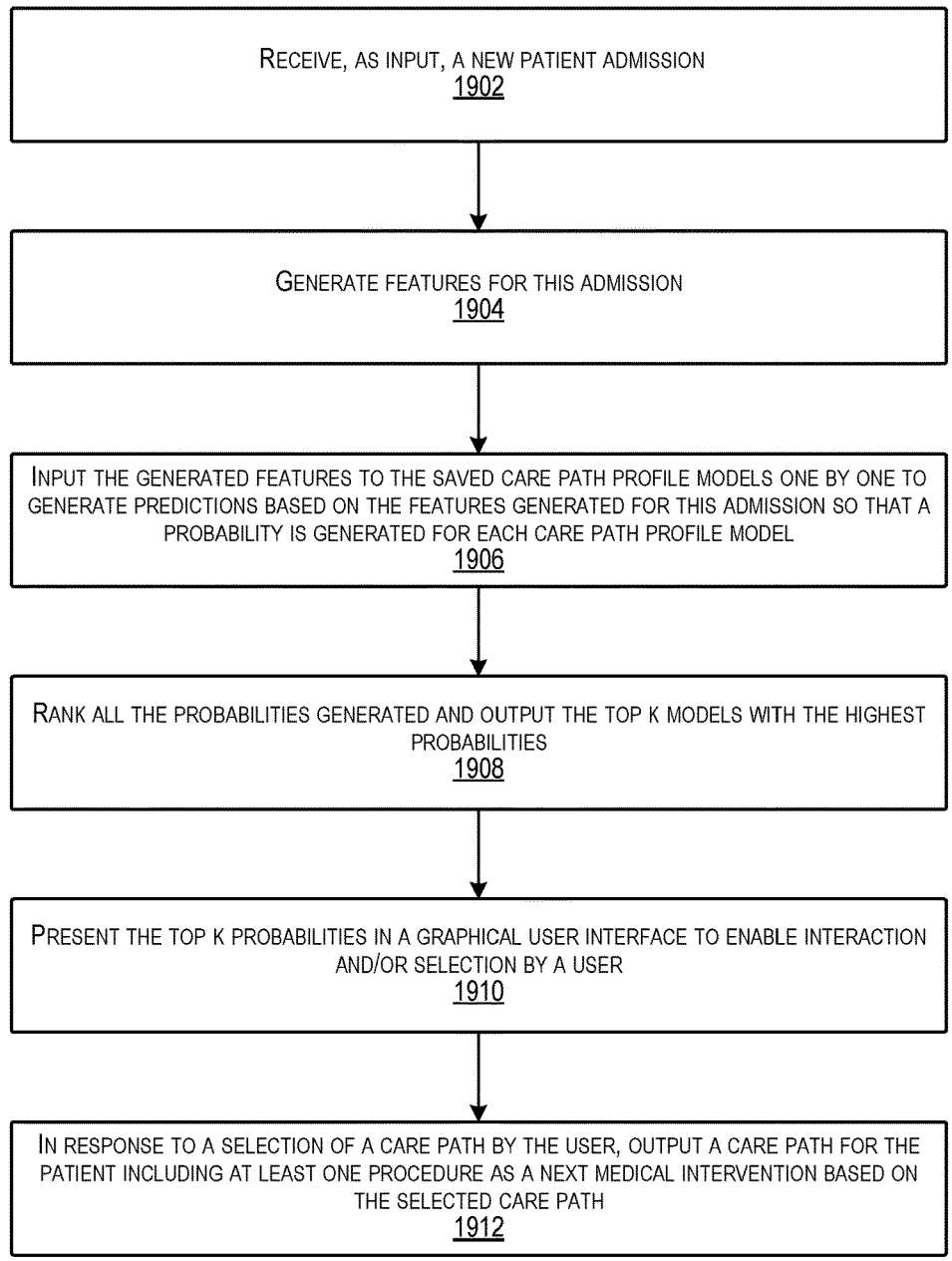
FIG. 19 is a flow diagram illustrating an example process for determining a next medical intervention according to some implementations.

FIG. 19 is a flow diagram illustrating an example process 1900 for determining a next medical intervention according to some implementations. In some examples, the process 1900 may be executed by the service computing device(s) 102 or other suitable computing device(s) by executing the next medical intervention recommendation application 192.

At 1902, the computing device may receive, as input, a new patient admission.

At 1904, the computing device may generate features for this admission. For example, the computing device may execute the feature generator 172 of the data mining program 122 to generate features for this admission as discussed above.

At 1906, the computing device may input the generated features to the saved care path patient profile models one by one to generate predictions based on the features generated for this admission. For example, the features generated from the received information related to the new patient admission may be inputted into the plurality of care path patient profile models to obtain a respective probability of being classified in a respective care path based on an amount of similarity to the patients who have gone through each care path. Accordingly, a probability is generated for each care path patient profile model.

At 1908, the computing device may rank all the probabilities generated and output the top k models with the highest probabilities.

At 1910, the computing device may present the top k probabilities in a GUI to enable interaction and/or selection by a user. An example GUI is described below with respect to FIG. 20.

At 1912, the computing device may receive, via the GUI, a user selection of a care path for the patient corresponding to the new patient admission, and may output the selected care path for the patient, including outputting at least one procedure as a next medical intervention for the patient, based on the selected care path.

Figure 20:
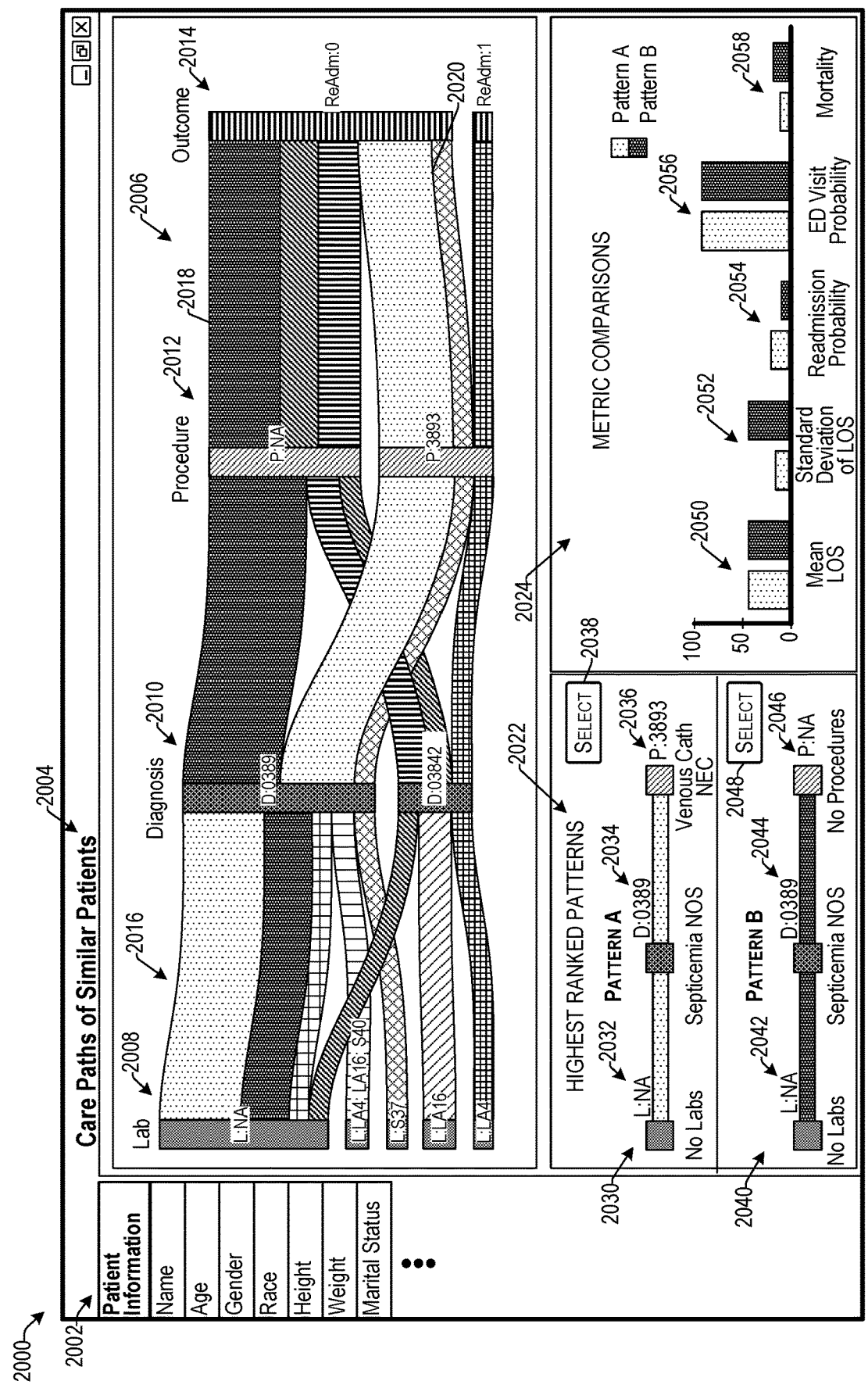
FIG. 20 illustrates an example GUI including a visualization of comparative effectiveness analysis for a next medical intervention according to some implementations.

FIG. 20 illustrates an example GUI 2000 including a visualization of comparative effectiveness analysis for a next medical intervention according to some implementations. In this example, the GUI 2000 includes patient information 2002, such as name, age, gender, etc. In addition, the GUI 2000 includes three areas that provide visualization of the results of the analysis performed by the care path analytics platform for the selected patient.

A first area 2004 shows the results for care paths for similar patients as a Sankey diagram 2006 showing the patterns of similar patients. For example, "similar" patients may refer to those with the same DRG code as the selected patient identified at 2002, although other matching characteristics may be used in other examples. The Sankey diagram progresses between a plurality of care path components, i.e., from lab 2008, to diagnosis 2010, to procedure 2012, to outcome 2014. A plurality of bands 2016 extend between each of these care path components and the relative heights of the bands may indicate the number of patients that experienced the respective care path component. For instance, the labs 2008 are divided into five different lab actions, i.e., L:NA (no lab work was performed); L:LA4, LA16, S40 (three different lab works were performed); L:S37 (a particular lab work indicated by code S37 was performed); L:LA16 (a particular lab work indicated by code LA16 was performed); and L:LA4 (a particular lab work indicated by code LA4 was performed).

One or more bands 2016 extend from each of the lab actions, and the relative heights of the bands may be based on the number of patients who experienced the same care path combination of components 2008, 2010, 2012 and 2014. In this example, only two diagnoses 2010 are included, namely a first diagnosis labeled with code D:0389 and a second diagnosis labeled with code D:03842. Furthermore, two procedures 2012 are depicted, namely, a first procedure P:NA in which no action was taken and a second procedure with code P:3893. Additionally, two outcomes 2014 are illustrated, i.e., no readmission (ReAdm:0) or readmission (ReAdm:1). In this example, a first band 2018 and a second band 2020 indicate the most likely care paths to result in no readmission, which may correspond to the highest ranking care paths identified above, e.g., in the process 1900 discussed with respect to FIG. 19.

The bottom left of the GUI 2000 includes an area 2022 including the two most likely care paths 2018 and 2020 based on care path patient profile models. Furthermore, the bottom right of the GUI 2000 includes an area 2024 visualizing comparisons of the associated metrics for the two most likely care paths 2018 and 2020. In this example, the most likely care path pattern is referred as pattern A, and the corresponding flow in the Sankey diagram may be highlighted as band 2020. In addition, the second most likely care path pattern is referred as pattern B and corresponds to band 2018 in the Sankey diagram.

Thus, in area 2022, for pattern A, the care path components may be presented in greater detail to include a description corresponding to the respective codes. For example, as indicated at 2030, care path pattern A includes lab→diagnosis→procedure in which the lab is L:NA, indicated to be No Labs, as indicated at 2032, the diagnosis is indicated to be D:0389 Septicemia NOS, as indicated at 2034, and the procedure is indicated to be P:3893 Venous Cath NEC, as indicated at 2036. As indicated at 2038, the user may click on, or otherwise select a virtual control to select pattern A if the user desires to apply the care path of pattern A to the selected patient. Similarly, as indicated at 2040 for care path pattern B, the lab is L:NA, indicated to be No Labs, as indicated at 2042, the diagnosis is indicated to be D:0389 Septicemia NOS, as indicated at 2044, and the procedure is indicated to be P:NA, No Procedures, as indicated at 2046. As indicated at 2048, the user may click on, or otherwise select a virtual control to select pattern B if the user desires to apply the care path of pattern B to the selected patient. As one example, a user selection of a particular care path for the patient may cause the next medical intervention recommendation application to output the selected care path for the patient, which may include outputting at least one procedure as a next medical intervention for the patient, based on the selected care path.

Additionally, the area 2024 showing the metric comparisons may include the five metrics discussed above with respect to the visualization of FIG. 15. Thus, the metrics in this example include mean LOS, as indicated at 2050, standard deviation of LOS, as indicated at 2052, readmission probability, as indicated at 2054, ED visit probability, as indicated at 2056, and mortality probability, as indicated at 2058. Furthermore, while a bar graph is used in this example, other types of visualizations may be used in other examples, such as the spider chart 1500 discussed above with respect to FIG. 15.

Figure 21:
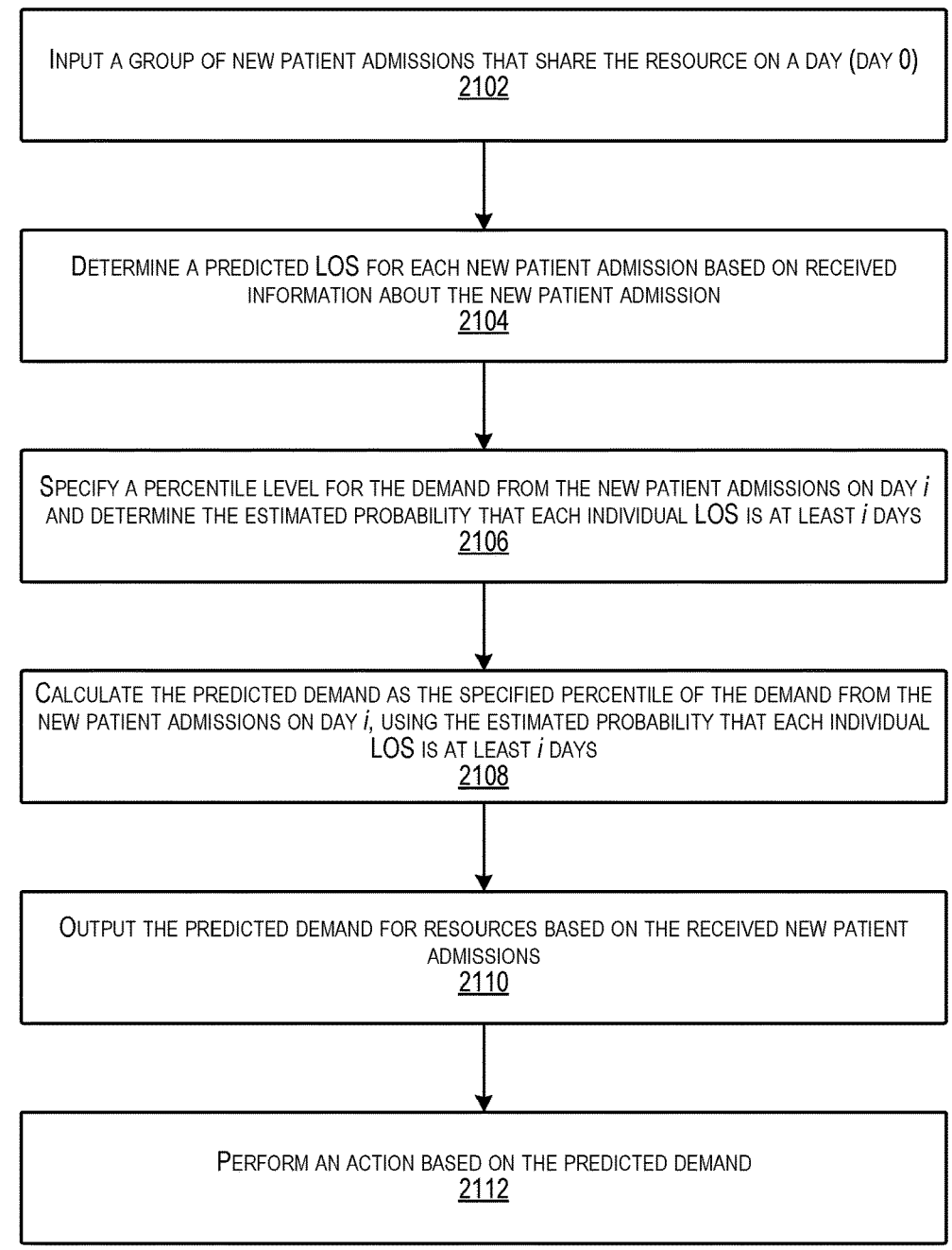
FIG. 21 is a flow diagram illustrating an example process for determining predicted resource utilization according to some implementations.

FIG. 21 is a flow diagram illustrating an example process 2100 for determining resource utilization according to some implementations. In some examples, the process 2100 may be executed by the service computing device(s) 102 or other suitable computing device(s), such as by executing one of the hospital bed management application 188 or the staff planning application 190.

At 2102, the computing device may receive, as input, a group of new patient admissions for a day (day 0) that share a resource.

At 2104, the computing device may determine a predicted LOS for each admission based on received information about the new patient admission. For example, the computing device may execute the LOS prediction application 186 discussed above with respect to FIG. 1 for each admission to determine the LOS distribution for each admission in the group.

At 2106, the computing device may specify a percentile level and determine the estimated probability that its LOS is at least i days. As one example, suppose there are a total of M new patients, then for each individual patient admission m, the estimated probability that its LOS is at least i may be $x_m(i)$.

At 2108, the computing device may calculate the specified percentile $D_i$ of the demand from the new patient admissions on day i. As one example, $D_i$ is the specified percentile of the sum of M independent binary (0/1) random variables with expected values $x_m(i)$, m=1, 2, . . . , M.

At 2110, the computing device may output the predicted demand $D_i$ for resources for one or more selected days i based on the received new patient admissions.

At 2112, the computing device may perform an action based on the predicted demand. For example, in the case that computing device is executing the hospital bed management application 188, the hospital bed management application 188 may be executed to reserve a required number of beds based on the predicted demand for the beds. Similarly, in the case that the staff planning application 190 is being executed, the staff planning application 190 may schedule a required number of staff employees to work at specified times based on the predicted demand for staffing at those times.

The example processes described herein are only examples of processes provided for discussion purposes. Numerous other variations will be apparent to those of skill in the art in light of the disclosure herein. Further, while the disclosure herein sets forth several examples of suitable frameworks, architectures and environments for executing the processes, the implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Various instructions, processes, and techniques described herein may be considered in the general context of computer-executable instructions, such as programs stored on computer-readable media, and executed by the processor(s) herein. Generally, programs include computer-readable instructions, routines, modules, applications, objects, components, data structures, executable code, etc., for performing particular tasks or implementing particular abstract data types. These programs and the like may be executed as native code or may be downloaded and executed, such as in a virtual machine or other just-in-time compilation execution environment. Typically, the functionality of the programs may be combined or distributed as desired in various implementations. An implementation of these programs and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed:

1. A system comprising:
a display;
one or more processors in communication with the display; and
one or more non-transitory computer-readable media maintaining executable instructions, which, when executed by the one or more processors, program the one or more processors to perform operations comprising:
generating a plurality of care path patient profile models based on:
identifying a plurality of care path patterns for a plurality of past patient admissions,
selecting a subset of the care path patterns having a frequency greater than a threshold,
generating respective sets of features for the care path patterns in the subset based at least in part on at least one of:
generating a feature vector for the care path patterns for the past patient admissions based on the associated care path pattern frequency, and determining a threshold on care path pattern frequency for each of the care path patterns in the subset to maximize mutual information between features in the feature vector and outcome labels for the plurality of past patient admissions for determining features in the sets of features, or
performing bi-clustering to cluster transitions in the care path patterns into clusters to use as the features of the sets of features, and
training a respective care path patient profile model as a trained classifier for each care path pattern in the subset using the respective sets of features;
receiving information related to a new patient admission;
generating features from the received information related to the new patient admission;
inputting the features generated from the received information related to the new patient admission into the plurality of care path patient profile models to obtain a respective probability of being classified in a respective care path based on an amount of similarity to the patients who have gone through each care path;

ranking respective care path patterns based on the respective probabilities to determine, for the new patient admission, at least one of: a likelihood of readmission, a likelihood of acquiring an infection, or a likely length of stay; and presenting, on the display, information related to at least one care path pattern in a graphical user interface (GUI) based on the ranking.

2. The system as recited in claim 1, wherein presenting information related to at least one care path pattern in the GUI based on the ranking comprises:

presenting information related to at least one highest ranked care path pattern, the information related to the at least one highest ranked care path pattern including lab information, diagnosis information, and procedure information.

3. The system as recited in claim 1, the operations further comprising:

receiving, via the GUI, a user selection of a care path pattern for a patient corresponding to the new patient admission; and outputting information related to the selected care path pattern for the new patient admission by outputting at least one procedure as a next medical intervention for the patient based on the selected care path pattern.

4. The system as recited in claim 1, the operations further comprising, based on inputting the features generated from the received information into the plurality of care path patient profile models, determining the likely length of stay for the new patient admission as at least one of:

an empirical distribution of length of stay of historical admissions associated with respective care path patterns; or a weighted mixture distribution of the length of stay determined based on determining a weight for individual care path patterns in the subset, determining the empirical distribution of the length of stay of historical admissions associated with the individual care path patterns, and determining the weighted mixture distribution from the empirical distribution and the determined weights.

5. The system as recited in claim 4, the operations further comprising:

determining at least one of the empirical distribution or the weighted mixture distribution as length stay distributions for a plurality of new patient admissions;

determining a demand for a hospital resource based on the determined length of stay distributions for the plurality of new patient admissions; and performing at least one scheduling action based on the determined demand.

6. The system as recited in claim 1, wherein generating the respective sets of features for the care paths in the subset based on generating the feature vector for the care path patterns for the past patient admissions comprises:

generating a binary feature vector as the feature vector for the past patient admissions based on the associated care path pattern frequency, assigning a first value if the associated care path pattern having a frequency over a first threshold, assigning a second value different from the first value otherwise;

determining the outcome labels for the plurality of past patient admissions; and determining an optimized threshold as the threshold on the care path pattern frequency for each of the care path patterns in the subset to maximize the mutual information between the binary feature vector and the outcome labels.

7. The system as recited in claim 1, wherein generating the respective sets of features for the care paths in the subset by performing bi-clustering comprises:

for each care path pattern in the subset of the care path patterns, selecting transitions in the care path pattern and generating at least one of a co-occurrence matrix of the two elements in each transition, a frequency matrix of the two elements in each transition, or a response rate matrix of the two elements in each transition;

performing bi-clustering on at least one of the respective co-occurrence matrix, the frequency matrix, or the response rate matrix to obtain respective bi-clusters; and generating the features for each respective patient admission corresponding to the care path pattern if the respective patient admission has gone through a transition corresponding to a bi-cluster.

8. A method comprising:

generating, by one or more processors, a plurality of care path patient profile models based on:

identifying, by the one or more processors, a plurality of care path patterns for a plurality of past patient admissions;

selecting, by the one or more processors, a subset of the care path patterns having a frequency greater than a threshold, generating, by the one or more processors, respective sets of features for the care path patterns in the subset based at least in part on at least one of:

generating, by the one or more processors, a feature vector for the care path patterns for the past patient admissions based on the associated care path pattern frequency, and determining a threshold on care path pattern frequency for each of the care path patterns in the subset to maximize mutual information between features in the feature vector and outcome labels for the plurality of past patient admissions for determining features in the sets of features, or performing, by the one or more processors, bi-clustering to cluster transitions in the care path patterns into clusters to use as the features of the sets of features, and training, by the one or more processors, a respective care path patient profile model as a trained classifier for each care path pattern in the subset using the respective sets of features;

receiving, by the one or more processors, information related to a new patient admission;

generating, by the one or more processors, features from the received information related to the new patient admission;

inputting, by the one or more processors, the features generated from the received information related to the new patient admission into the plurality of care path patient profile models to obtain a respective probability of being classified in a respective care path based on an amount of similarity to the patients who have gone through each care path; and presenting, by the one or more processors, on a display, information related to at least one care path pattern in a graphical user interface (GUI).

9. The method as recited in claim 8, wherein presenting information related to at least one care path in the GUI comprises:
   ranking respective care path patterns based on the respective probabilities; and
   presenting information related to at least one highest ranked care path, the information related to the at least one highest ranked care path including lab information, diagnosis information, and procedure information.

10. The method as recited in claim 8, further comprising:
    receiving, via the GUI, a user selection of a care path pattern for a patient corresponding to the new patient admission; and
    outputting information related to the selected care path pattern for the new patient admission by outputting at least one procedure as a next medical intervention for the patient based on the selected care path pattern.

11. The method as recited in claim 8, wherein generating the respective sets of features for the care paths in the subset by generating the feature vector comprises:
    generating a binary feature vector as the feature vector for the past patient admissions based on the associated each care path pattern frequency, assigning a first value if the associated care path pattern having a frequency over a first threshold, assigning a second value different from the first value otherwise;
    determining the outcome labels for the plurality of past patient admissions; and
    determining an optimized threshold on care path pattern frequency for each of the care path patterns in the subset to maximize the mutual information between the binary feature vector and the outcome labels.

12. The method as recited in claim 8, further comprising based on inputting the features generated from the received information into the plurality of care path patient profile models, determining the likely length of stay for the new patient admission as at least one of:
    an empirical distribution of length of stay of historical admissions associated with respective care path patterns; or
    a weighted mixture distribution of the length of stay determined based on determining a weight for individual care path patterns in the subset, determining the empirical distribution of the length of stay of historical admissions associated with the individual care path patterns, and determining the weighted mixture distribution from the empirical distribution and the determined weights.

13. The method as recited in claim 12, further comprising:
    determining at least one of the empirical distribution of the weighted mixture distribution as the length stay distributions for a plurality of new patient admissions;
    determining a demand for a hospital resource based on the determined length of stay distributions for the plurality of new patient admissions; and
    performing at least one scheduling action based on the determined demand.

14. One or more non-transitory computer-readable media storing instructions which, when executed by one or more processors, program the one or more processors to perform operations comprising:
    generating a plurality of care path patient profile models based on:
        identifying a plurality of care path patterns for a plurality of past patient admissions;
        selecting a subset of the care path patterns having a frequency greater than a threshold,
        generating respective sets of features for the care path patterns in the subset based at least in part on at least one of:
            generating a feature vector for the care path patterns for the past patient admissions based on the associated care path pattern frequency, and determining a threshold on care path pattern frequency for each of the care path patterns in the subset to maximize mutual information between features in the feature vector and outcome labels for the plurality of past patient admissions for determining features in the sets of features, or
            performing bi-clustering to cluster transitions in the care path patterns into clusters to use as the features of the sets of features, and
        training a respective care path patient profile model as a trained classifier for each care path pattern in the subset using the respective sets of features;
    receiving information related to a new patient admission;
    generating features from the received information related to the new patient admission;
    inputting the features generated from the received information related to the new patient admission into the plurality of care path patient profile models to obtain a respective probability for each of the care path patient profile models as to whether the new patient admission is classified therein; and
    based at least in part on the respective probability, presenting, on a display, information related to at least one care path pattern in a graphical user interface (GUI).

15. The one or more non-transitory computer-readable media as recited in claim 14, wherein presenting information related to at least one care path in the GUI comprises:
    ranking respective care path patterns based on the respective probabilities to determine, for the new patient admission, at least one of: a likelihood of readmission, a likelihood of acquiring an infection, or a likely length of stay; and
    presenting information related to at least one highest ranked care path, the information related to the at least one highest ranked care path including lab information, diagnosis information, and procedure information.

16. The one or more non-transitory computer-readable media as recited in claim 15, the operations further comprising:
    receiving, via the GUI, a user selection of a care path pattern for a patient corresponding to the new patient admission; and
    outputting information related to the selected care path pattern for the new patient admission by outputting at least one procedure as a next medical intervention for the patient based on the selected care path pattern.

17. The one or more non-transitory computer-readable media as recited in claim 14, the operations further comprising based on inputting the features generated from the received information into the plurality of care path patient profile models, determining a probability of a length of stay for the new patient admission as at least one of:
    an empirical distribution of length of stay of historical admissions associated with respective care path patterns; or
    a weighted mixture distribution of the length of stay determined based on determining a weight for individual care path patterns in the subset, determining the empirical distribution of the length of stay of historical admissions associated with the individual care path patterns, and determining the weighted mixture distribution from the empirical distribution and the determined weights.

18. The one or more non-transitory computer-readable media as recited in claim 17, the operations further comprising:
- determining at least one of the empirical distribution or the weighted mixture distribution as length of stay distributions for a plurality of new patient admissions;
- determining a demand for a hospital resource based on the determined length of stay distributions for the plurality of new patient admissions; and
- performing at least one scheduling action based on the determined demand.

\* \* \* \* \*